(12) United States Patent
Carrel et al.

(10) Patent No.: US 9,526,837 B2
(45) Date of Patent: Dec. 27, 2016

(54) AUTOMATIC INJECTION DEVICE

(71) Applicant: Becton Dickinson France, Le Pont de Claix (FR)

(72) Inventors: Franck Carrel, Le Pont de Claix (FR); Lionel Maritan, Pierre-Chatel (FR); Frederic Perot, Saint Paul de Varces (FR)

(73) Assignee: Becton Dickinson France, Le Pont-de-Claix (FR)

( * ) Notice: Subject to any disclaimer, the term of this patent is extended or adjusted under 35 U.S.C. 154(b) by 53 days.

(21) Appl. No.: 14/426,304

(22) PCT Filed: Aug. 28, 2013

(86) PCT No.: PCT/IB2013/002348
§ 371 (c)(1),
(2) Date: Mar. 5, 2015

(87) PCT Pub. No.: WO2014/037802
PCT Pub. Date: Mar. 13, 2014

(65) Prior Publication Data
US 2015/0202368 A1    Jul. 23, 2015

(30) Foreign Application Priority Data
Sep. 5, 2012   (EP) .................................... 12306060

(51) Int. Cl.
*A61M 5/00*     (2006.01)
*A61M 5/20*     (2006.01)
(Continued)

(52) U.S. Cl.
CPC .......... *A61M 5/2033* (2013.01); *A61M 5/3204* (2013.01); *A61M 5/326* (2013.01);
(Continued)

(58) Field of Classification Search
CPC ............... A61M 2005/206; A61M 2005/3142; A61M 5/3204; A61M 2005/2073
(Continued)

(56) References Cited

U.S. PATENT DOCUMENTS 8,696,628 B2    4/2014    Grunhut
2010/0312195 A1    12/2010    Johansen et al.
(Continued)

FOREIGN PATENT DOCUMENTS

JP    2012504009 A    2/2012
WO    2009062508 A1    5/2009

*Primary Examiner* — Kevin C Sirmons
*Assistant Examiner* — Deanna K Hall
(74) *Attorney, Agent, or Firm* — The Webb Law Firm

(57) ABSTRACT

The present invention relates to an automatic injection device (1) comprising: a container (2) having a longitudinal axis A and movable between a first position and a second position, in which the needle is inserted, biasing means (8), for moving the container to its second position, retaining means (70, 74, 74*b*) for maintaining said biasing means in a first stressed state, triggering means (90, 91*e*) for releasing said retaining means, said retaining means comprising a lever member having a rotatable cylinder part and a radial projection extending therefrom, said radial projection being in a first angular position when said retaining means is in its passive condition, said radial projection being in a second angular position, different from said first angular position, when said retaining means is in its active condition, said rotatable cylinder part being included in a transversal plane of said longitudinal axis A.

29 Claims, 20 Drawing Sheets

Figures 1A, 1B, 1C:
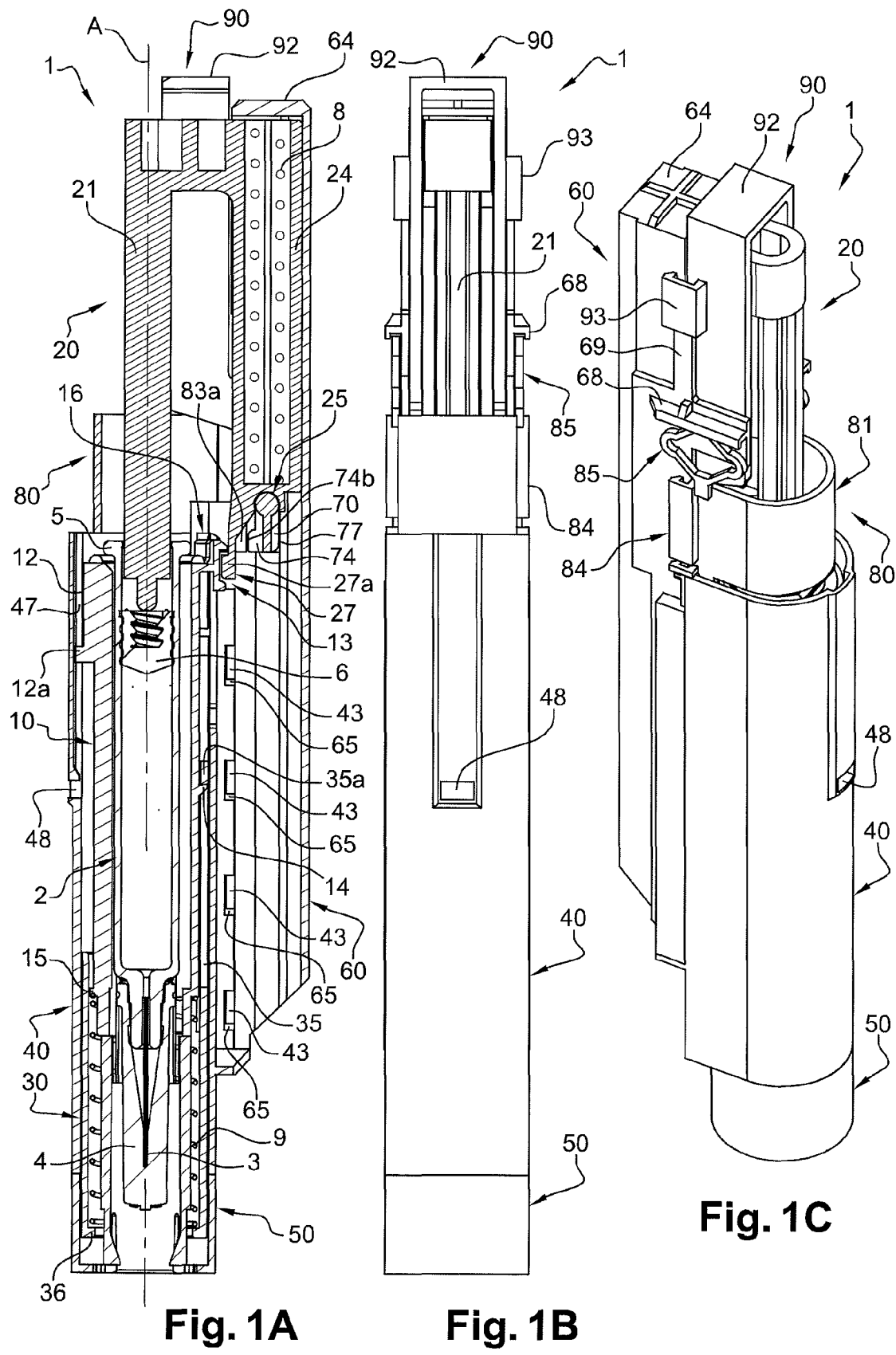

(51) Int. Cl.
  *A61M 5/32* (2006.01)
  *A61M 5/50* (2006.01)
  *A61M 5/31* (2006.01)

(52) U.S. Cl.
  CPC ..... *A61M 5/5086* (2013.01); *A61M 2005/206* (2013.01); *A61M 2005/3104* (2013.01); *A61M 2005/3142* (2013.01); *A61M 2005/3143* (2013.01); *A61M 2205/581* (2013.01); *A61M 2205/582* (2013.01); *A61M 2205/583* (2013.01)

(58) Field of Classification Search
  USPC ........................................................ 604/187
  See application file for complete search history.

(56) References Cited

U.S. PATENT DOCUMENTS

2011/0028910 A1  2/2011  Weber
2011/0092915 A1  4/2011  Olson et al.
2011/0224621 A1  9/2011  Johansen et al.

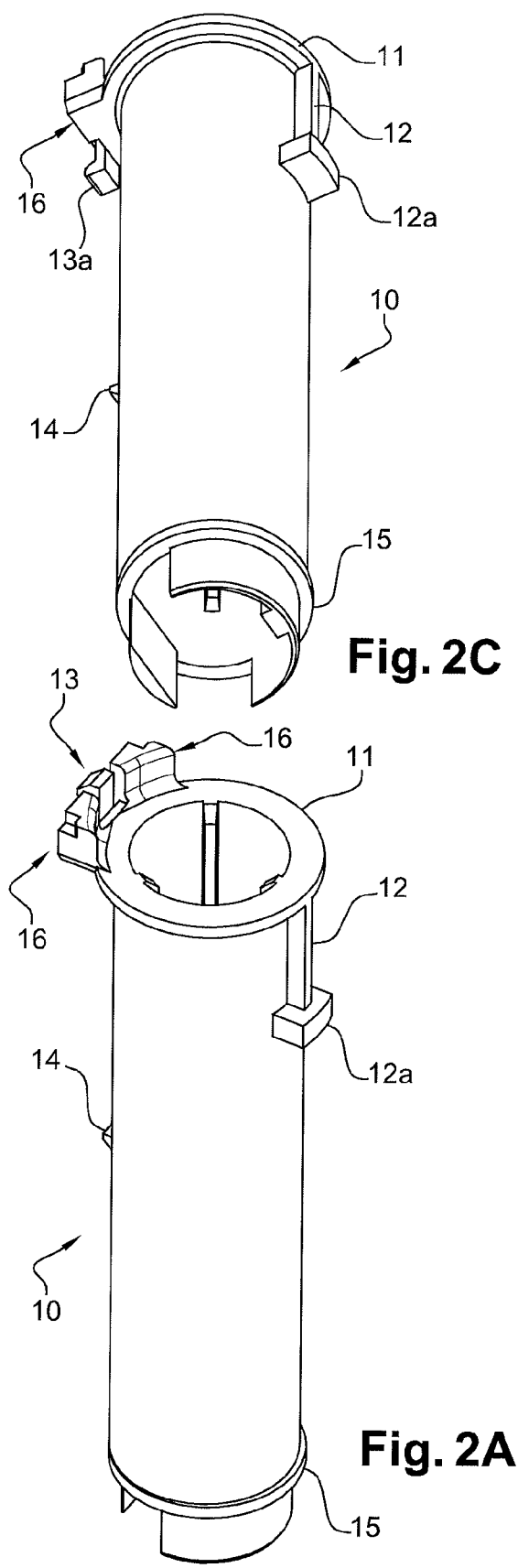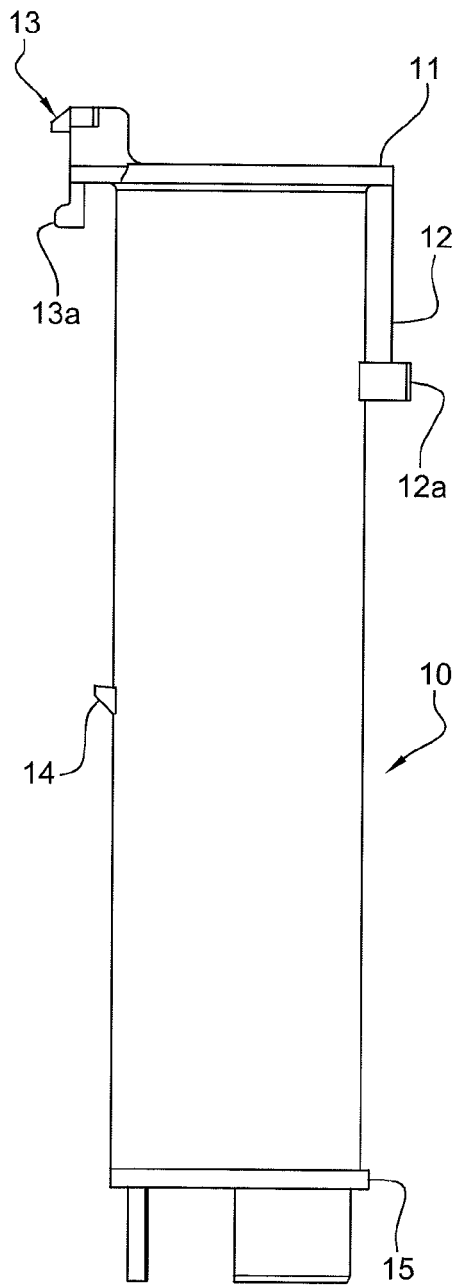
Fig. 2C
Fig. 2A
Fig. 2B

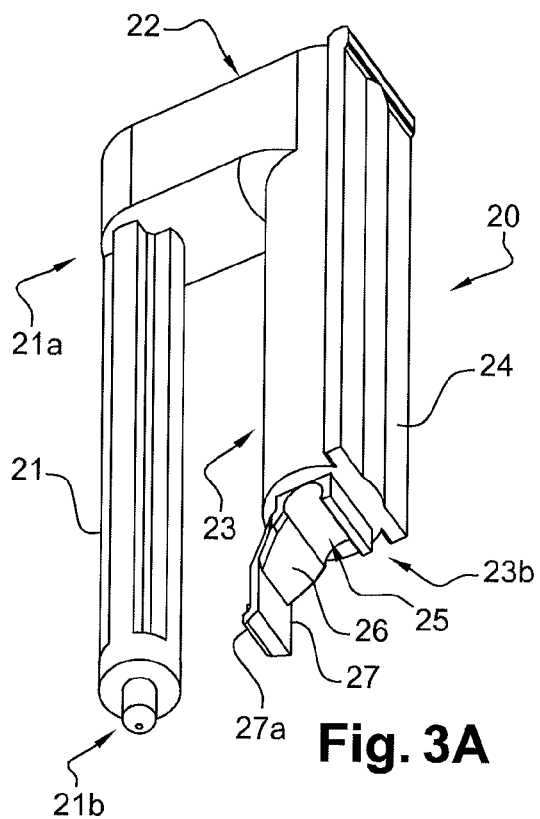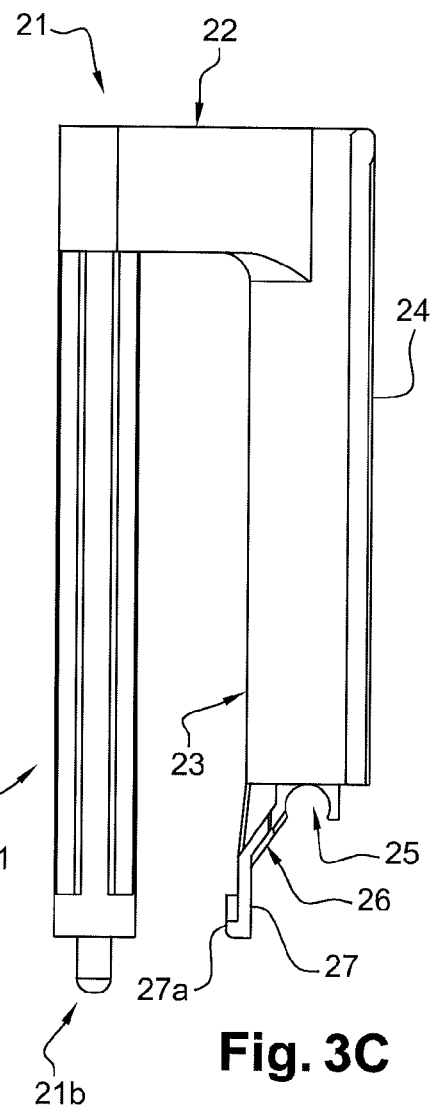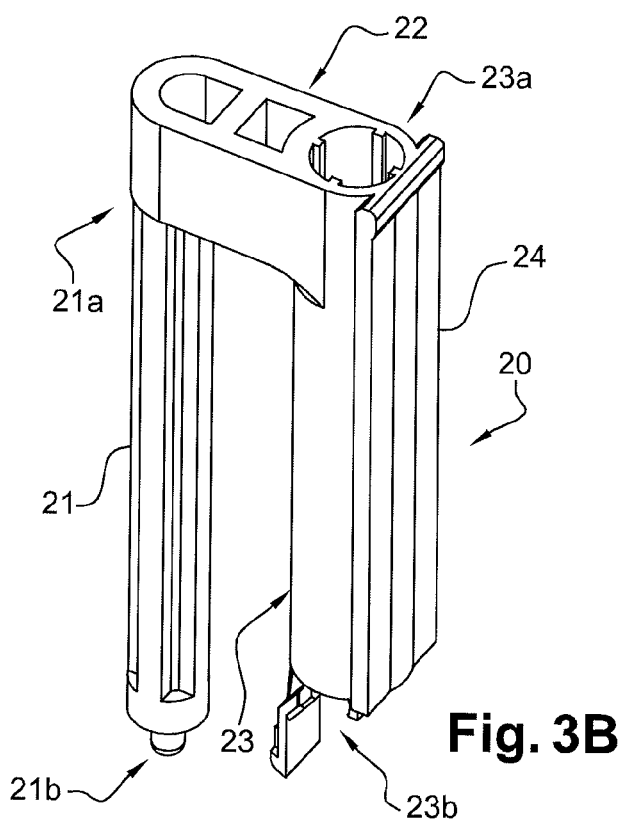

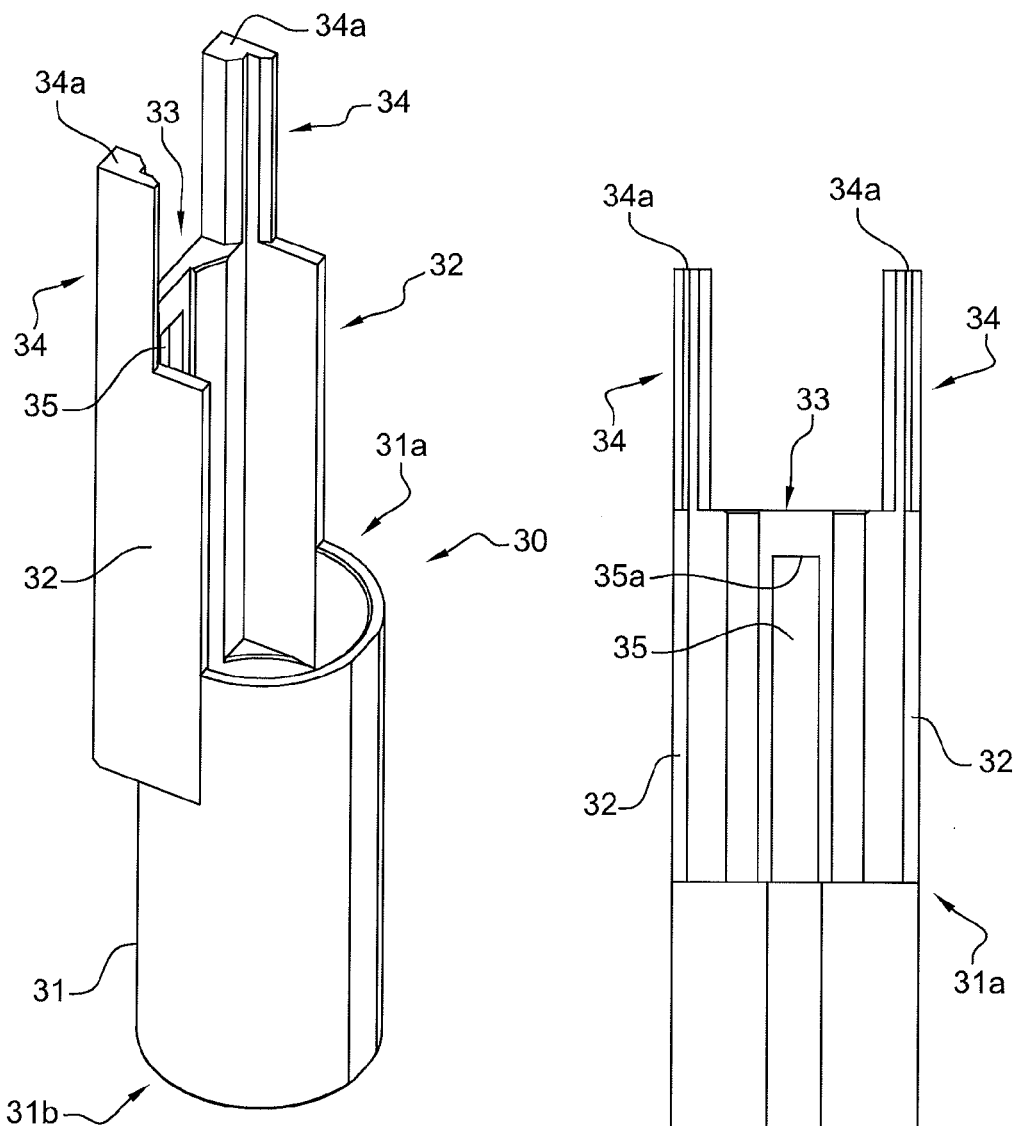
Fig. 4A
Fig. 4B
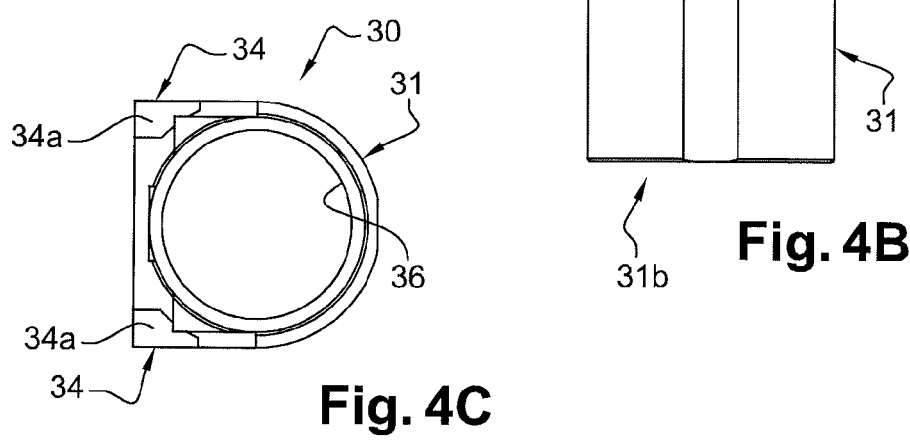
Fig. 4C

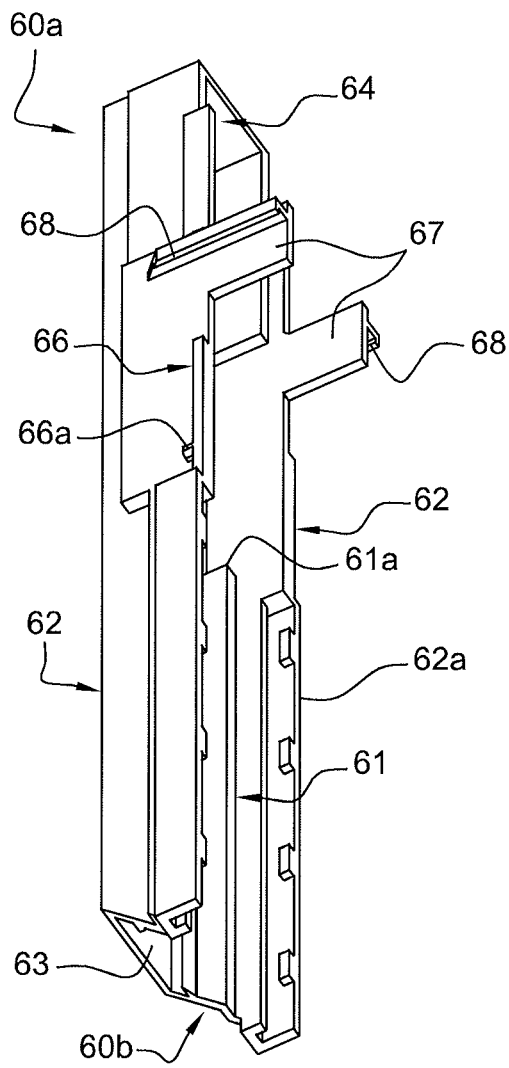
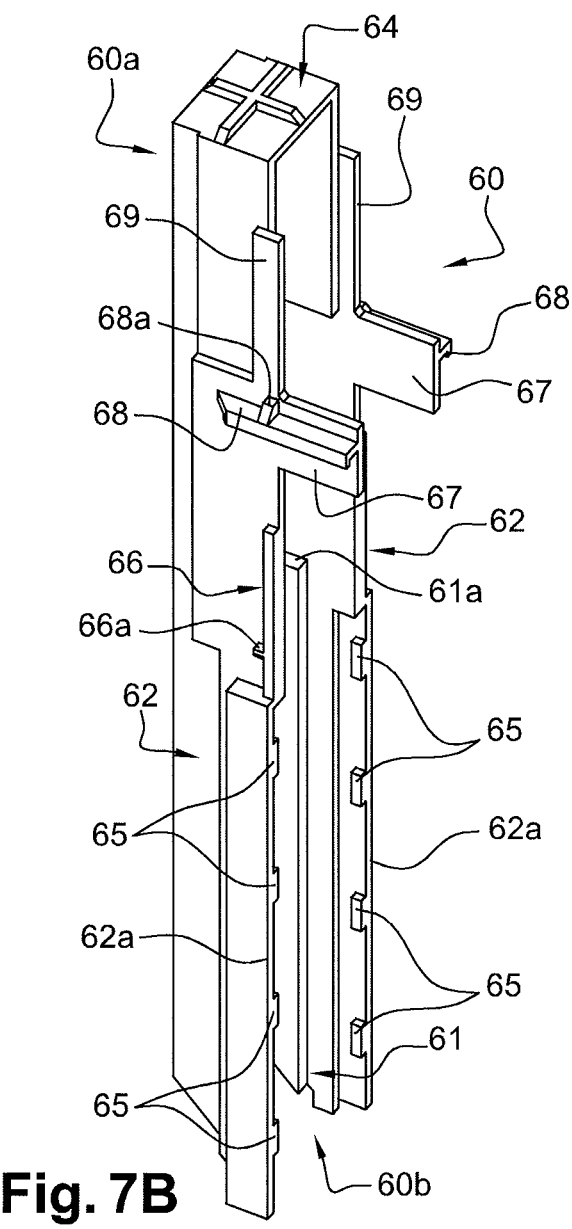
Fig. 7A
Fig. 7B

Fig. 16A  Fig. 16B  A-A

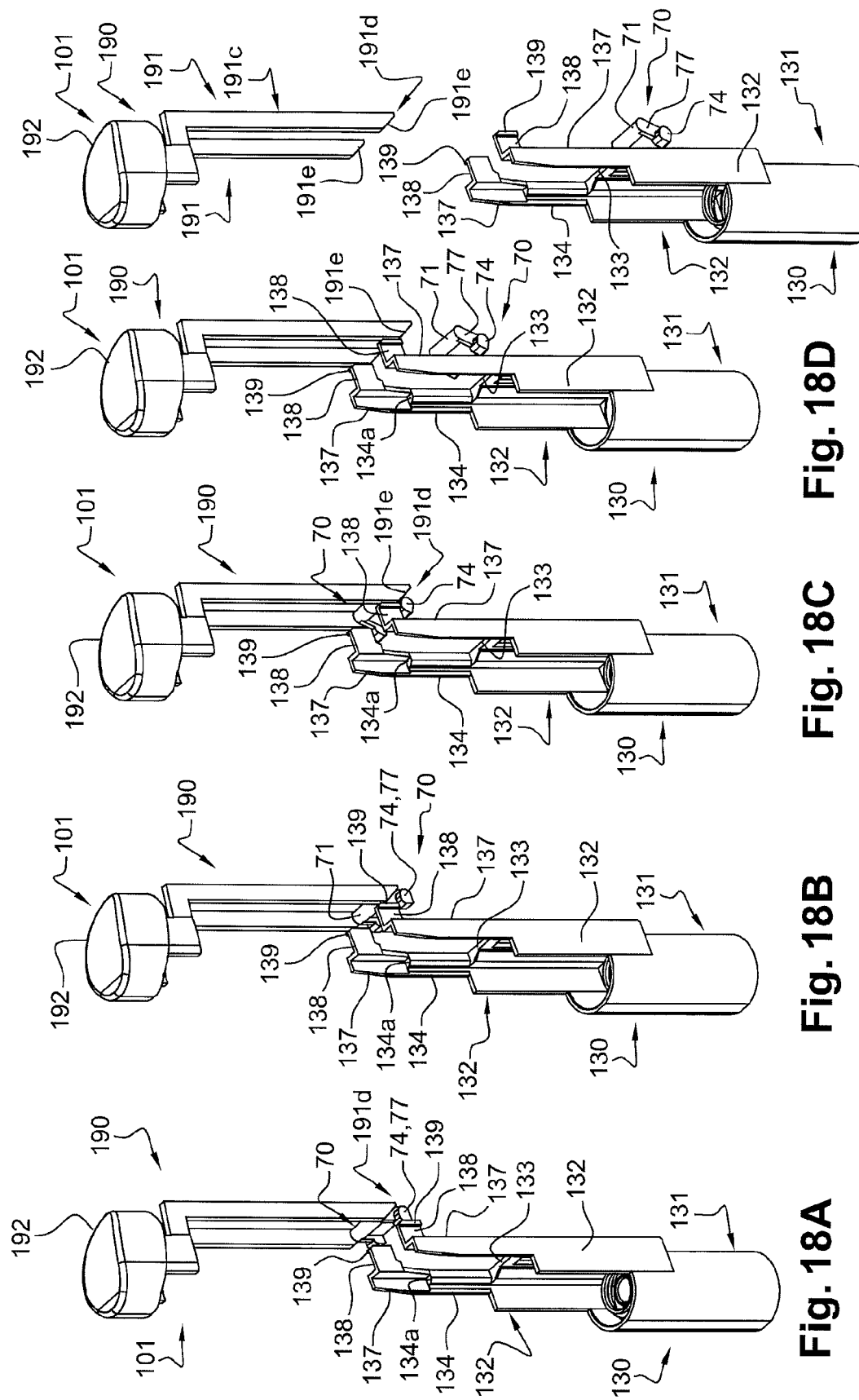

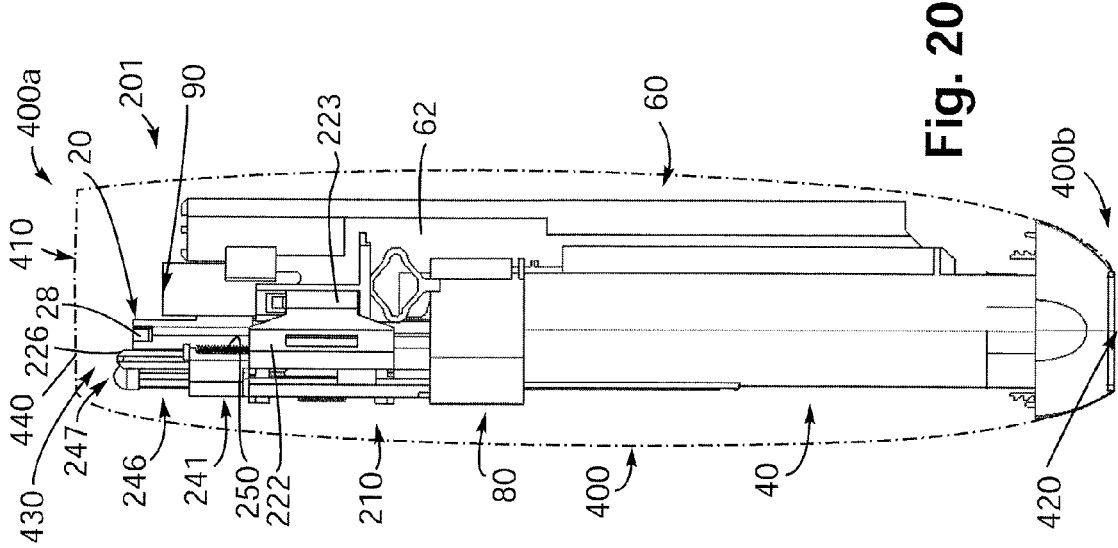

AUTOMATIC INJECTION DEVICE

CROSS-REFERENCE TO RELATED APPLICATIONS

This application is the United States national phase of International Application No. PCT/IB2013/002348 filed Aug. 28, 2013, and claims priority to European Patent Application No. 12306060.0 filed Sep. 5, 2012, the disclosures of which are hereby incorporated in their entirety by reference.

The present invention relates to a device for injection of a product, for which the insertion step of the needle is automated and may be completed with minimal effort from the user.

In this application, the distal end of an element or of a device means the end furthest away from the hand of the user and the proximal end means the end closest to the hand of the user, when the element or device is in the use-position. Similarly, in this application, the terms "in the distal direction" and "distally" mean in the direction of the injection, and the terms "in the proximal direction" and "proximally" mean in the direction opposite to the direction of injection.

Devices for automatic injection of a product, also called autoinjectors, are widely used in medical fields where the treatment of a pathology requires daily injections, such as the treatment of some diabetes, and where patients often proceed to these injections on their own. As patients are not professional healthcare workers, the whole process is as much as possible automated so that the patient needs not make decisions during the injection. Autoinjectors usually comprise on one hand a container having a needle and filled with the product to be injected, such as a prefilled syringe for example, and on the other hand a motor part, in other words a part comprising the various systems which will trigger the insertion of the needle, realise the injection and potentially activate a protection system at the end of injection.

Most of the already existing autoinjectors comprise at least a system for automatically inserting the needle into the patient's skin, and triggering means for initiating such an insertion of the needle, the triggering means being intended to be activated by the patient when he is ready. Nevertheless, most of the automatic insertion systems of the autoinjectors of the prior art require substantial effort from the user. For example, those automatic insertion systems may involve deflection of one or more flexible parts of the autoinjector, or they may imply overcoming a resisting force between two parts of the autoinjector, in such a way that the patient needs to apply a high force on the autoinjector at the time he wishes to activate the triggering means. The high force necessary for activating the triggering means may hurt the user. It may also cause the user to be reluctant to proceed to the injection, or to be puzzled, not knowing if he should continue the injection or not.

It is therefore important that at least the insertion of the needle into the injection site, which is the first step to take place in the injection process, be simplified and proceed softly and smoothly with no opportunity for the user to face anxiety. In this view, it is important that the user needs not apply too high a force on the device at the time he is ready to activate the triggering means for proceeding to the insertion step of the needle into the site of injection.

In addition, many autoinjectors of the prior art are designed so that the container, such as a syringe for example, is assembled into the device during the manufacture of the motor part, pieces of the motor part and of the container being connected together in an intricate way. Proceeding this way means that, once a motor part is designed for a syringe of a certain volume capacity and prefilled with a specified drug, it is not possible to use the same motor part for another type of syringe or for another drug.

Nevertheless, for the pharmaceutical companies, it would be advantageous to prepare on one hand the prefilled syringe, and on the other hand the motor part of the autoinjector, and then assemble the prefilled syringe onto the motor part of the autoinjector, without having to redesign the motor part each time the type of syringe is changed or each time the drug is replaced by another drug with different properties, for example with a different viscosity.

Autoinjectors have been proposed, for which at least a part of the motor part is positioned laterally with respect to the syringe.

Nevertheless, such autoinjectors still need to be improved in particular with respect to the safety system intended to protect the needle at the end of injection, and to prevent access to said needle as soon as possible after the injection is completed. In this view, it is important to preserve the security of the user and that the needle be not accessible to the user, even in case the user misuses the device, for example by removing it from the injection site before the injection is completed.

In addition, as mentioned before, as users of these autoinjectors are usually not professional healthcare workers, it is desirable that not only the insertion step, but the whole process of the injection, from insertion of the needle into the injection site to withdrawal of the device from the injection site and disposal of the device proceeds softly and smoothly with no opportunity for the user to face anxiety.

Such devices for automatic injection must prove to be very simple to use and very safe. In particular, it is important to ensure that a controlled dose of a product is injected with such a device, that is to say a complete injection must be performed. Moreover, in some cases, the user may withdraw the device for automatic injection before the injection is completed. It is therefore important for the user to be informed that the product has been substantially completely injected and that he may withdraw the device from the injection site.

A first aspect of the invention is a device for injection of a product into an injection site, said device comprising:

a housing having a longitudinal axis A and receiving a container for the product to be injected, said container being aligned on said longitudinal axis, said container being substantially closed at a proximal end by a stopper, said stopper being capable of being moved distally within said container so as to expel the product to be injected, and at a distal end by a needle for the exit of the product to be injected, said container being movable with respect to said housing between a first position, in which the needle does not extend beyond a distal end of the housing, and a second position, distally spaced with respect to said first position, in which the needle extends beyond the distal end of the housing, biasing means, coupled to said container and to said housing at least from said first position to said second position of the container, designed for exerting a distal force on said container so as to move said container from its first position to its second position when going from a first state to a second state, said second state being less stressed than said first state, retaining means coupled to said container and to said housing in the first position of the container, for releasably maintaining said biasing means in its first state, said retaining means being capable of moving from a passive condition, in which it maintains said biasing means in its first state, to an active condition, in which said biasing means is free to expand to its second state, triggering means capable of moving said retaining means from its passive condition to its active condition, wherein said retaining means comprise a lever member having a rotatable cylinder part and at least a radial projection extending from said cylinder part, said radial projection being in a first angular position when said retaining means is in its passive condition, said radial projection being in a second angular position, different from said first angular position, when said retaining means is in its active condition, said rotatable cylinder part being included in a transversal plane of said longitudinal axis A.

The arrangement of the device of the invention allows a patient to proceed to the insertion step of the needle with no substantial effort: indeed, as will appear from the description below, the retaining means of the device of the invention comprise a rotatable cylinder part that is included in a transversal plane of said longitudinal axis A. The release of these retaining means, and thereby the freeing of the biasing means intended to cause the insertion of the needle, imply a partial rotation of this rotatable cylinder part, this rotation being caused by cooperation of the triggering means with such cylinder part. Contrary to the autoinjectors of the prior art, thanks to the arrangement of this rotatable cylinder part in a transversal plane of the longitudinal axis of the container, the cooperation of the retaining means with the triggering means for freeing the biasing means require only little force. The user needs therefore not to apply the device of the invention with a high force on his skin at the time he wishes to activate the triggering means in order to initiate the insertion of the needle.

In particular, because of the arrangement of the retaining means of the device of the invention requiring little effort for initiating the insertion step, it is possible to provide the device of the invention with biasing means having a high force. Indeed, thanks to the arrangement of the retaining means of the device of the invention, the effort required for beginning the insertion step will remain the same regardless from the force of the biasing means. Moreover, in the embodiments in which the biasing means also serve for pushing distally the stopper, via a plunger rod or not, during the injection step, it is possible to provide the device with biasing means showing a high intrinsic force. For example, when the product to be injected shows a high viscosity, the device of the invention may be provided with biasing means having a high intrinsic force allowing said biasing means to automatically realize both the insertion step and the injection step, while the effort required from the user at the beginning of the process in order to initiate the insertion step remains low.

In embodiments, said biasing means is a spring linked to said stopper via a plunger rod, said device further comprising releasable maintaining means for maintaining said container fixed with respect to said plunger rod when said spring goes from its first state to its second state, said maintaining means being released when said spring reaches its second state.

In embodiments, said maintaining means comprise a hook fixed with respect to said container, said hook trapping a rim located on said plunger rod, the rim being allowed to escape from said hook under the force of the spring only once said container has reached its second position and said spring is in its second state.

Such embodiments enhance the safety of the device as they ensure the injection may not start before the needle is correctly inserted at the injection site.

In embodiments, the cylinder part of the lever member being rotatably received within a recess of said plunger rod, said radial projection is engaged within an abutment surface fixed with respect to said housing when said radial projection is in its first angular position, said radial projection being disengaged from said abutment surface when said radial projection is in its second angular position.

In embodiments, said triggering means comprises a button mounted in sliding translation with respect to said housing, said button comprising a pushing surface accessible to a user for pushing on said button, said button further comprising a sloped surface capable of cooperating with said radial projection for rotating said cylinder part and moving said radial projection from its first angular position to its second angular position, when a user pushes on said pushing surface.

In embodiments, in its first angular position, the radial projection extends in the distal direction. Only very little force is therefore required for tilting the radial projection, i.e. for moving the radial projection out of its first angular position.

In embodiments, said button is mounted in sliding translation with respect to said housing along a direction parallel to said longitudinal axis A, said sloped surface thereby moving said radial projection out of the distal direction towards its second angular position when cooperating with said radial projection. Only little force is required from the user for pushing the sloped surface as the user may benefit from natural gravitational force for completing this step.

In embodiments, the device further comprises locking means for preventing said triggering means from moving said retaining means from its passive condition to its active condition, said locking means being releasable, and deactivating means for releasing the locking means.

The device of the invention is therefore very safe as it cannot be triggered before having neutralized the security system formed by the releasable locking means.

In embodiments, the locking means comprise a movable surface of said device, said surface being movable between a first position, in which it faces said radial projection so as to prevent cooperation between said radial projection and said sloped surface, to a second position, in which in it is released and no more faces said radial projection, thereby allowing cooperation between said radial projection and said sloped surface.

In embodiments, said deactivating means being capable of going from a storage position, in which it does not release the locking means, to an active position in which it releases the locking means and the triggering means may be activated, the device further comprises storage elastic return means for urging said deactivating means back in its storage position as long as the triggering means have not been activated.

Such an embodiment allows the user to apply the device at another location on the skin after having already tried a first location and even released the locking means at this first location. As long as the triggering means have not been activated, the step of releasing the locking means is reversible.

In embodiments, the device further comprises fixing means for maintaining said container in its second position with respect to said housing, and urging means coupled to said stopper and to said housing when said container is in its second position, said urging means being designed for distally moving said stopper when going from a first state to a second state, said second state being less stressed than said first state, thereby realizing injection of the product.

The device of the invention is therefore entirely automated, as both the insertion step and the injection step are automatically completed by means of the biasing means and of the urging means. The user is therefore ensured that these two steps proceed optimally, as he does not have to manually complete them.

In embodiments, said spring being further capable of going from its second state to a third state, during which said spring moves the stopper distally, said third state being less stressed than said second state, said spring forms both said biasing means and said urging means.

Such an embodiment allows to manufacture a compact device as only one spring is required for automatically performing two steps, namely an insertion step, during which the needle is inserted into the injection site, and an injection step, during which the product to be injected is actually delivered to the injection site.

In embodiments, the fixing means comprise a peg fixed with respect to said container and a window located on said housing, said peg being locked within said window when said container is in its second position with respect to said housing.

In embodiments, the device further comprises needle protection means, at least partially received within said housing, and movable with respect to said housing when said container is fixed in its second position with respect to said housing between an insertion position, in which a distal tip of the needle extends beyond the distal end of the needle protection means, and a final position, in which the distal tip of the needle does not extend beyond the distal end of the needle protection means, and elastic return means, coupled to said needle protection means and to said container, and designed for automatically moving said needle protection means from its insertion position to its final position, upon removal of the device from an injection site by a user.

The device of the invention therefore requires no particular effort from the user, is of simple use and perfectly safe: once the needle has been inserted into the injection site, as soon as the user withdraws the device from the injection site, the needle protection is triggered, and the needle is immediately rendered inaccessible to the user. In addition, in case the user misuses the device and withdraws it from the injection site before the injection is actually completed, the needle protection is nevertheless triggered. Actually, as soon as the needle is inserted in the injection site, the removal of the device from the injection will automatically trigger the needle protection. The device of the invention is therefore very comfortable for the user, in particular where the user is not a professional healthcare worker, as the user knows the used needle will never come in contact with his hand or fingers, regardless of how he performs the injection step.

In embodiments, in the first position of the container with respect to the housing, said needle protection means being movable with respect to said housing between a storage position and a use position, said use position being proximally spaced with respect to said storage position, at least part of said needle protection means forms said deactivating means.

The device of the invention is therefore easy to use, as it simply requires that the user applies the device on the skin of the patient and moves the housing with respect to the needle protection means in order to release the locking means.

In embodiments, at least part of said needle protection means further forms said locking means. The contact between the different cooperating parts of the device is therefore minimized and much lower force is required for triggering the insertion step.

In embodiments, said biasing means being positioned so as to produce a distal force along an axis parallel to said longitudinal axis A, said device further comprises a linking member coupled to said biasing means and to said container, said linking member being shaped and dimensioned so as to transmit said distal force to said container. By "axis parallel to the longitudinal axis A" is meant in the present application, an axis having the same direction as the longitudinal axis A, in other words, oriented along the distal-proximal direction, but separate, for example laterally spaced, from said longitudinal axis A. As will appear later in the description, such a location of the biasing means allows the device of the invention to be manufactured in two steps.

For example, a motor part of the device, comprising the biasing means, the retaining means, the triggering means and the urging means may be assembled on one hand. On another hand, the housing part may be assembled separately, said housing part comprising the housing, the deactivating means, the fixing means, the needle protection means and the elastic return means. The locking means may alternatively be part either of the motor part or of the housing part. Each part, namely the motor part on one hand and the housing part on the other hand, is autonomous before it is connected to the other part, and may be transported and/or handled on its own. This allows pharmaceutical companies for example to prefill the container, for example a syringe, of the housing with the drug to be injected on a first site, and then to assemble the motor part later on. In particular, thanks to the arrangement of the device of the invention, it is not necessary to redesign the motor part each time the type of syringe is changed or each time the drug is replaced by another drug with different properties, for example with a different viscosity.

In embodiments, said plunger rod forms said linking member, said plunger rod comprising a shaft aligned on said longitudinal axis A, said shaft being provided at its distal end with said stopper, a bridge linking a proximal end of said shaft to a proximal end of a lateral tubular lodging parallel to said longitudinal axis A and receiving said spring, said spring being in distal abutment on a distal transversal wall of said tubular lodging and being in proximal abutment on a proximal transversal wall fixed with respect to said housing. For example, the bridge extends in a radial direction with respect to the longitudinal axis A and the lateral tubular lodging has a longitudinal axis which parallel to the longitudinal axis A. The plunger rod may therefore have a global U-shape.

In embodiments, the recess of said plunger rod is located on a distal face of said distal transversal wall of said tubular lodging. Such embodiments allow positioning the radial projection of the lever member in the distal direction in its first angular position.

In embodiments, the device further comprises controlling means designed for producing a sensitive indication when said stopper reaches a distal end of said container.

Such embodiments allow the user, even if he is not a professional healthcare worker, to be informed that the correct dose of product has been injected and that he may withdraw the device from the injection with no risk that an incorrect dose has been injected.

In embodiments, the device further comprises temporizing means designed for delaying the production of said sensitive indicator once said stopper has reached a distal end of said container, thereby ensuring that indication to the user that injection of the product is completed is given only once the product is substantially expelled from the container.

Such embodiments provide for an additional warranty that all the dose of the product has been injected and that the user may not remove the device from the injection site too early.

In embodiments, the temporizing means comprise a holder fixed with respect to said housing and a sensitive indicator movable with respect to said holder between a distal position, in which it does not produce said sensitive indication, and a proximal position, in which it produces said sensitive indication, said temporizing means further comprising:

indicator biasing means coupled to said holder and to said sensitive indicator, designed for urging said sensitive indicator in its proximal position when going from a compressed state to an expanded state, indicator retaining means for maintaining said indicator biasing in their compressed state, wherein said indicator retaining means are released by cooperation of said indicator retaining means with at least a part of said plunger rod at the end of the injection step.

In embodiments, the device further comprises an outer shell surrounding the whole device, said outer shell being provided with at least a first hole for access to the triggering means by the user, and at least a second hole for exit of the needle and optionally of the needle protection means. Such embodiments enhance the comfort for the patient/user who is not confronted to the multiple parts and arrangement of the device.

In embodiments, at least a part of the sensitive indicator interacts with at least a part of a wall of said outer shell, when said sensitive indicator is in its proximal position, in order to produce said sensitive indication.

For instance, a part of the sensitive indicator may come in contact with a part of a wall of the outer shell, thereby producing a sound. A part of a wall of the outer shell may be made in transparent material, and a part of the sensitive indicator may come in regards to said transparent part, thereby producing a visual indication to the user that the device may be removed from the injection site. A part of a wall of the outer shell may comprise a window in which a part of the sensitive indicator may enter, thereby producing a tactile indication.

In embodiments, the device further comprises a removable distal cap for closing the distal end of said housing before use, said device further comprises tamper evident means for informing the user that the distal cap has already been removed at least once before having been replaced on said distal end of said housing.

In embodiments, the device further comprises dampening means for reducing the rate with which said container moves from its first position to its second position, under the effect of said biasing means. Such embodiments allow reducing the effect of the shock felt on his skin by the patient when the needle is inserted into the injection site, thereby making the device more comfortable for the patient.

In embodiments, the device of the invention is under the form of two autonomous connectable parts, namely a motor part and a housing part, said motor part comprising at least said biasing means, said retaining means, said triggering means, and said urging means, said housing part comprising at least said housing, said deactivating means, said fixing means, said needle protection means and said elastic return means, said locking means being located on one of said motor part and housing part said device further comprising connecting means for connecting said motor part to said housing part at time of use.

As seen above, the arrangement of the various parts of the device of the invention, and in particular the fact that the biasing means and the urging means are located laterally with respect to the longitudinal axis of the housing, allow to treat, transport, and/or handle the motor part on one hand, and the housing part on the other hand, before connecting these two parts. This is advantageous for pharmaceutical companies which fill the container of the housing independently from the motor part. In addition, thanks to the arrangement of the device of the invention allowing said device to be under the form of two connectable parts, it is not necessary to redesign the motor part each time the type of syringe/container is changed or each time the drug is replaced by another drug with different properties.

In embodiments, said locking means being located on said housing part, said motor part further comprises a temporary lock, for maintaining the retaining means in its passive condition when said motor part is not connected to said housing part, said temporary lock being removed from said motor part once said motor part is connected to said housing part, said temporary lock being then replaced by said locking means present on the housing part. For example, in such embodiments, said locking means comprises at least a surface of said needle protection means.

Figure 5A:
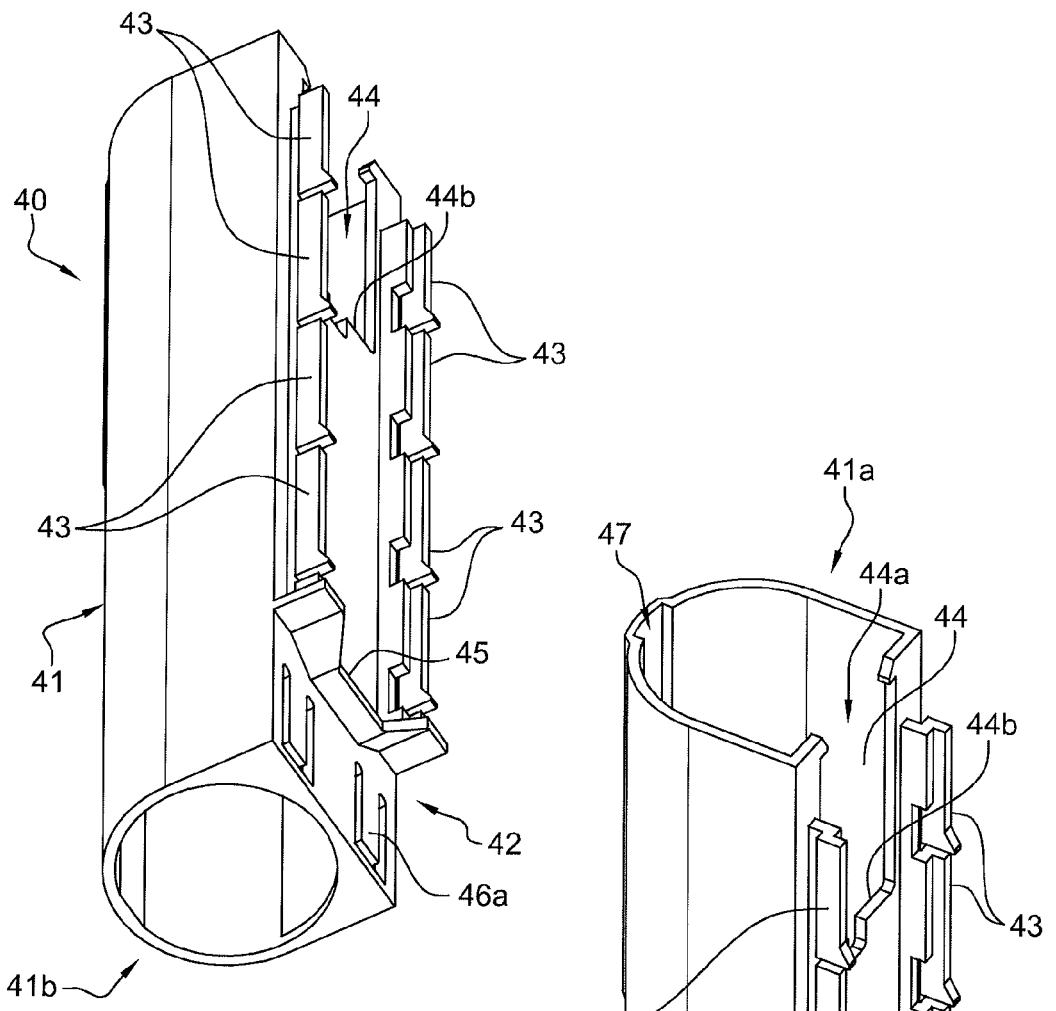
Figure 5B:
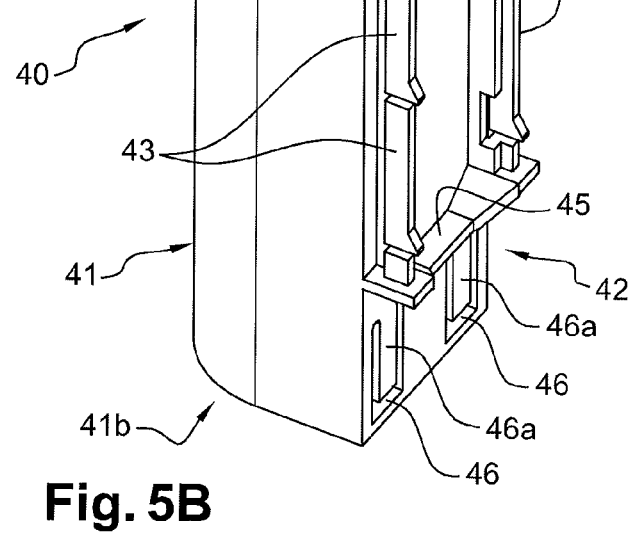
Figure 6A:
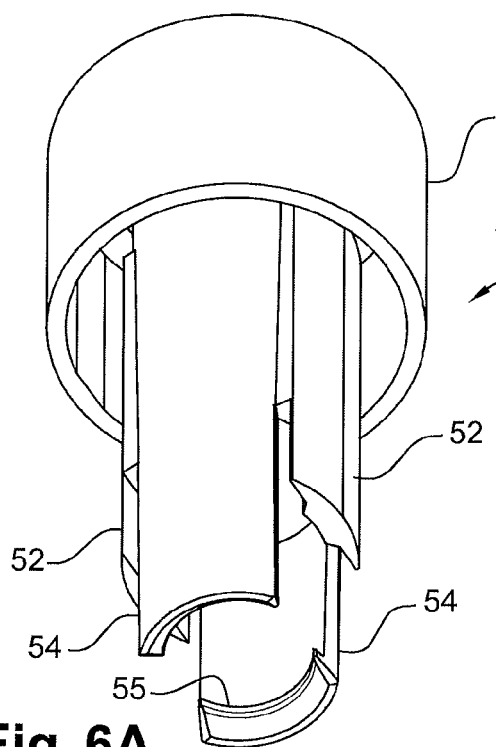
Figure 6C:
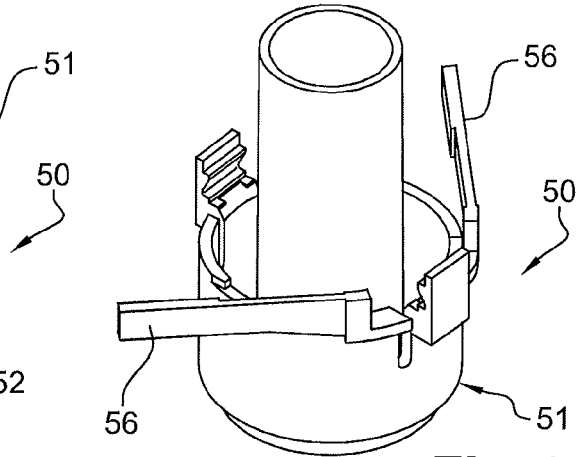
Figure 6D:
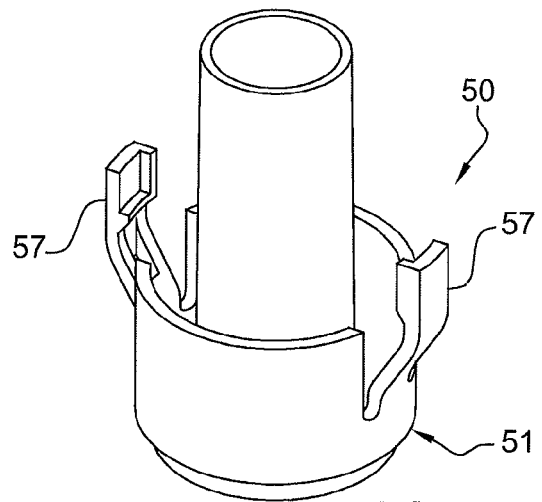
Figure 6B:
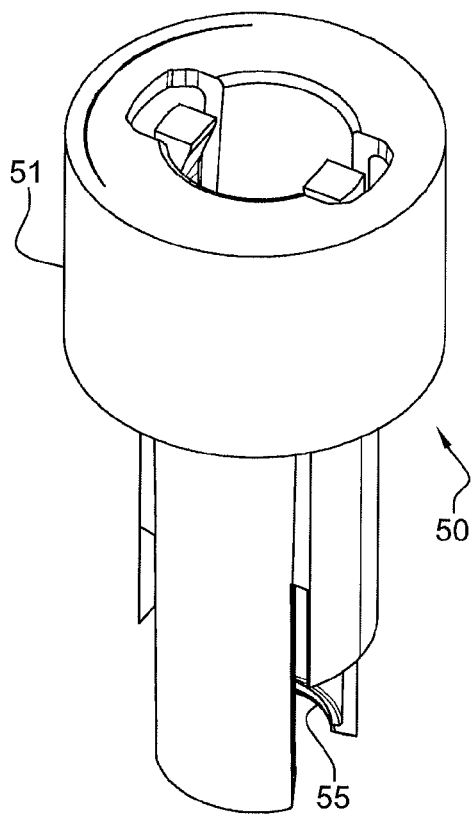
Figure 6E:
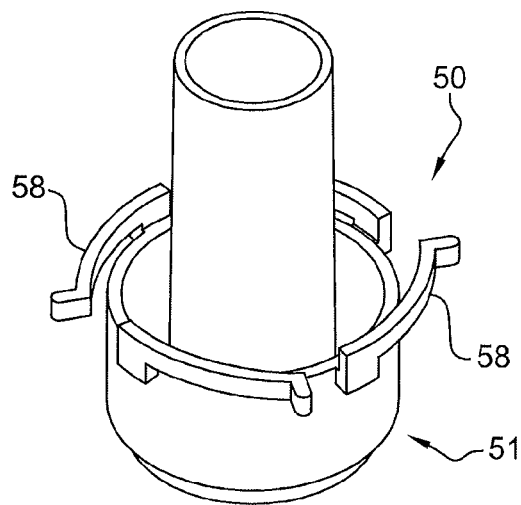
Figure 9A:
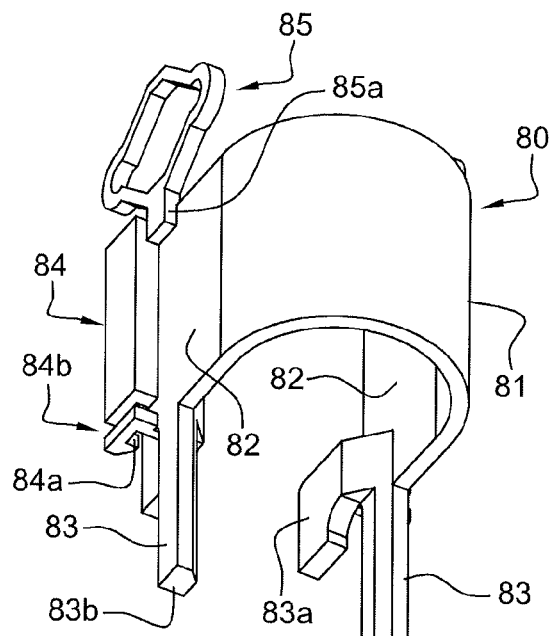
Figure 9B:
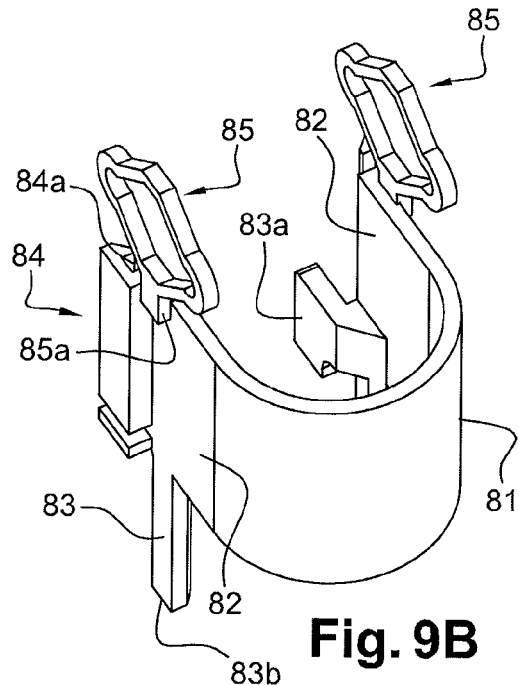
Figure 9C:
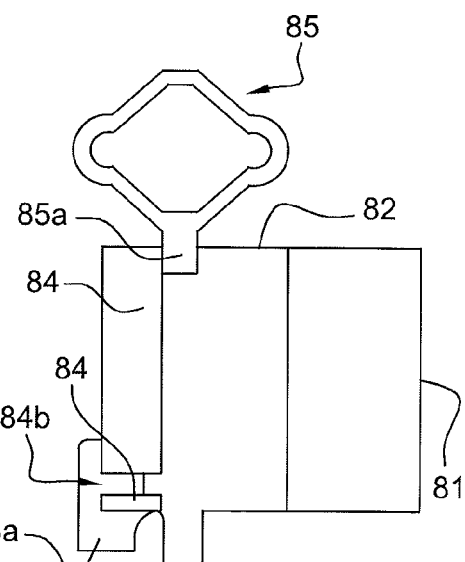
Figure 8:
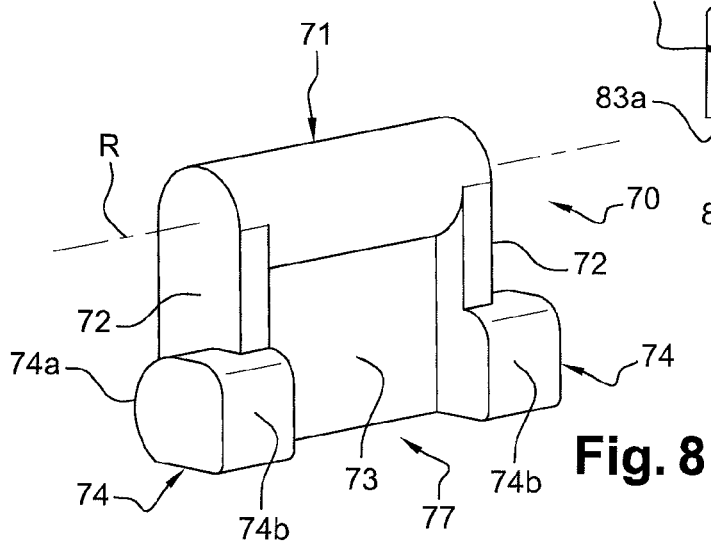
Figure 10:
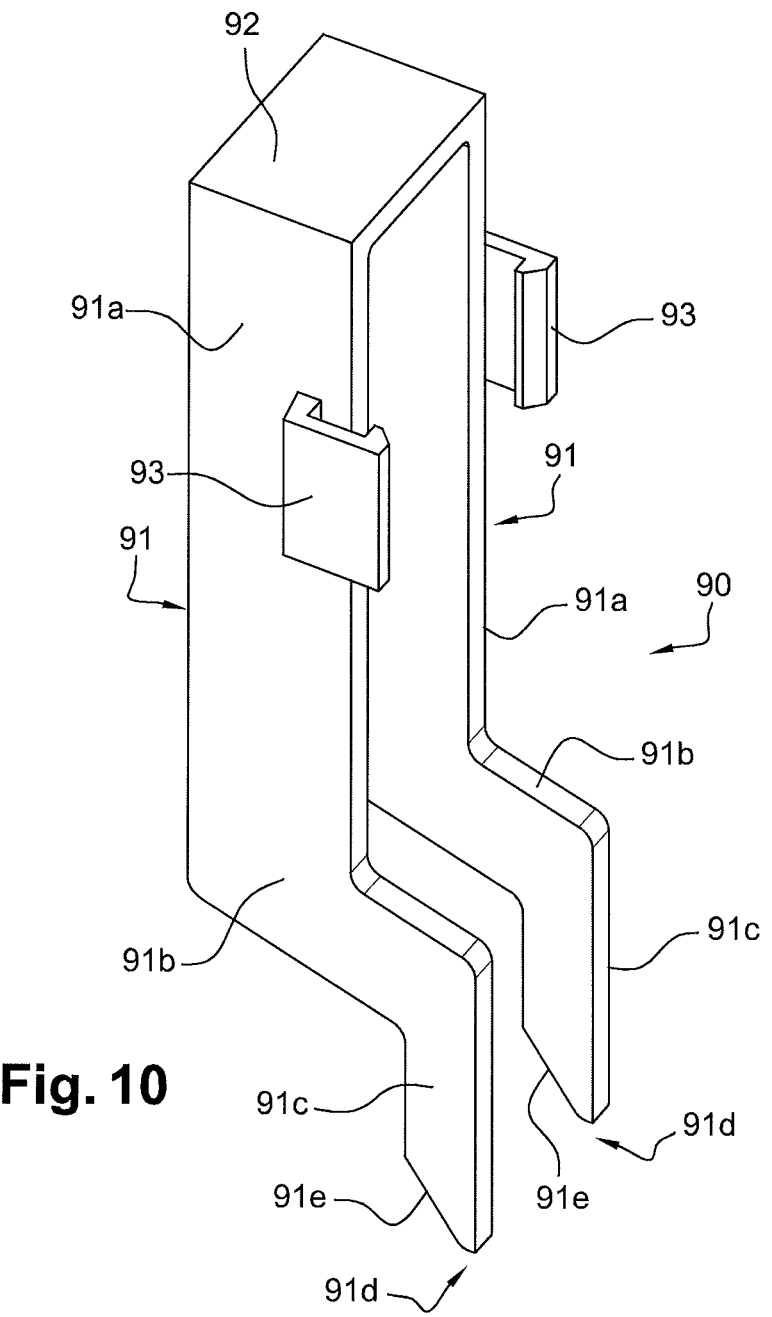
Figures 11A, 11B, 11C:
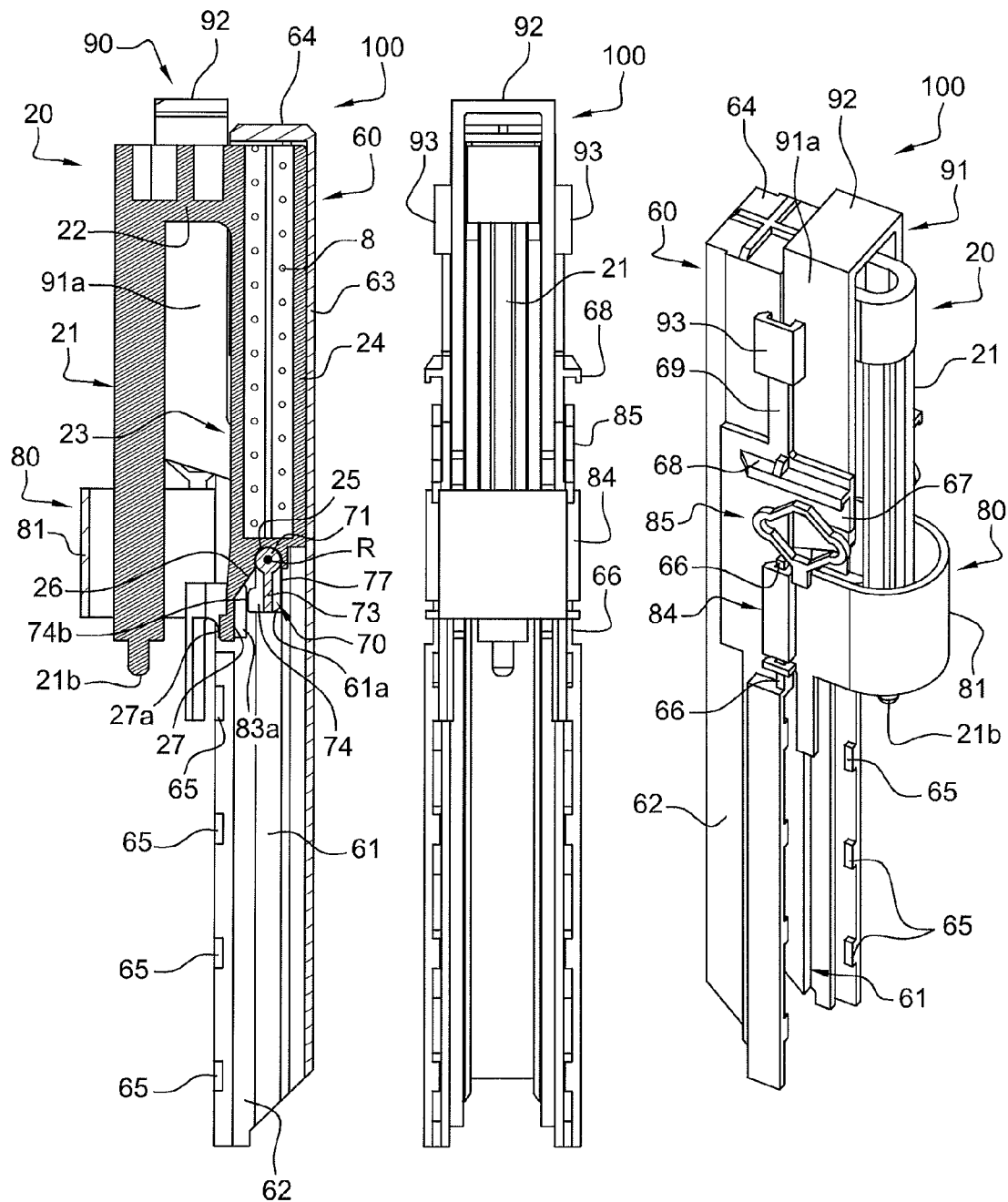
Figure 12A:
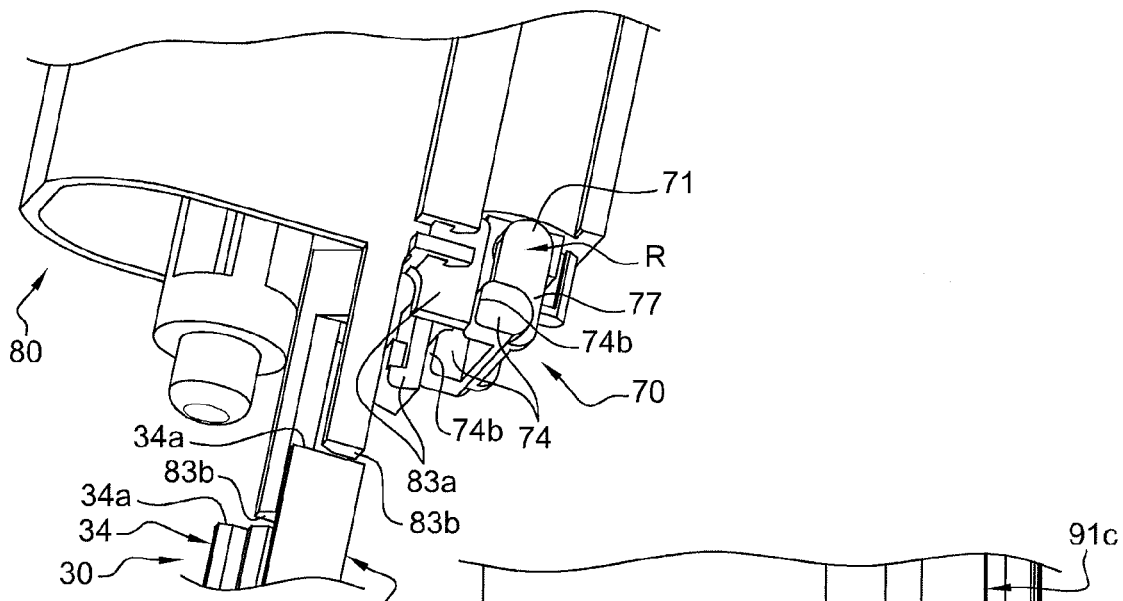
Figure 12B:
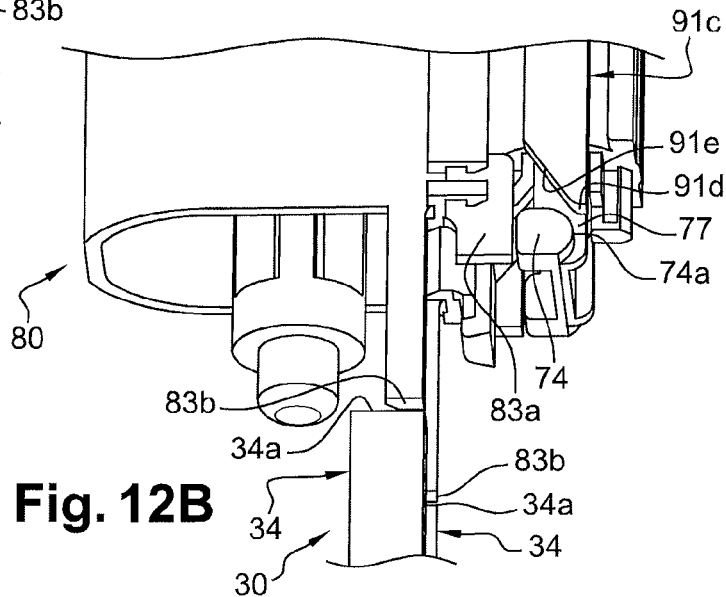
Figure 14A:
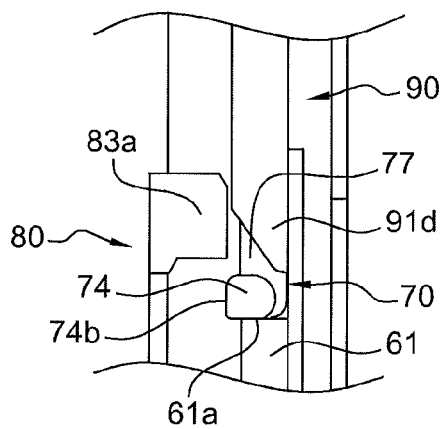
Figure 14B:
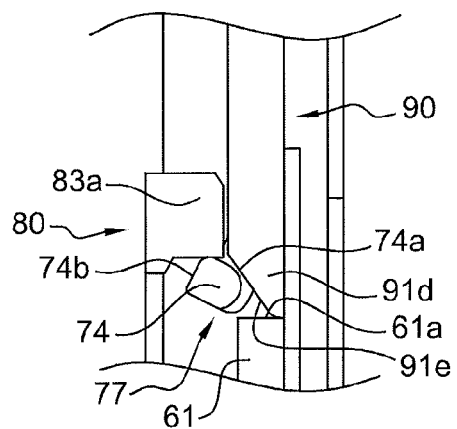
Figures 13A, 13B, 13C:
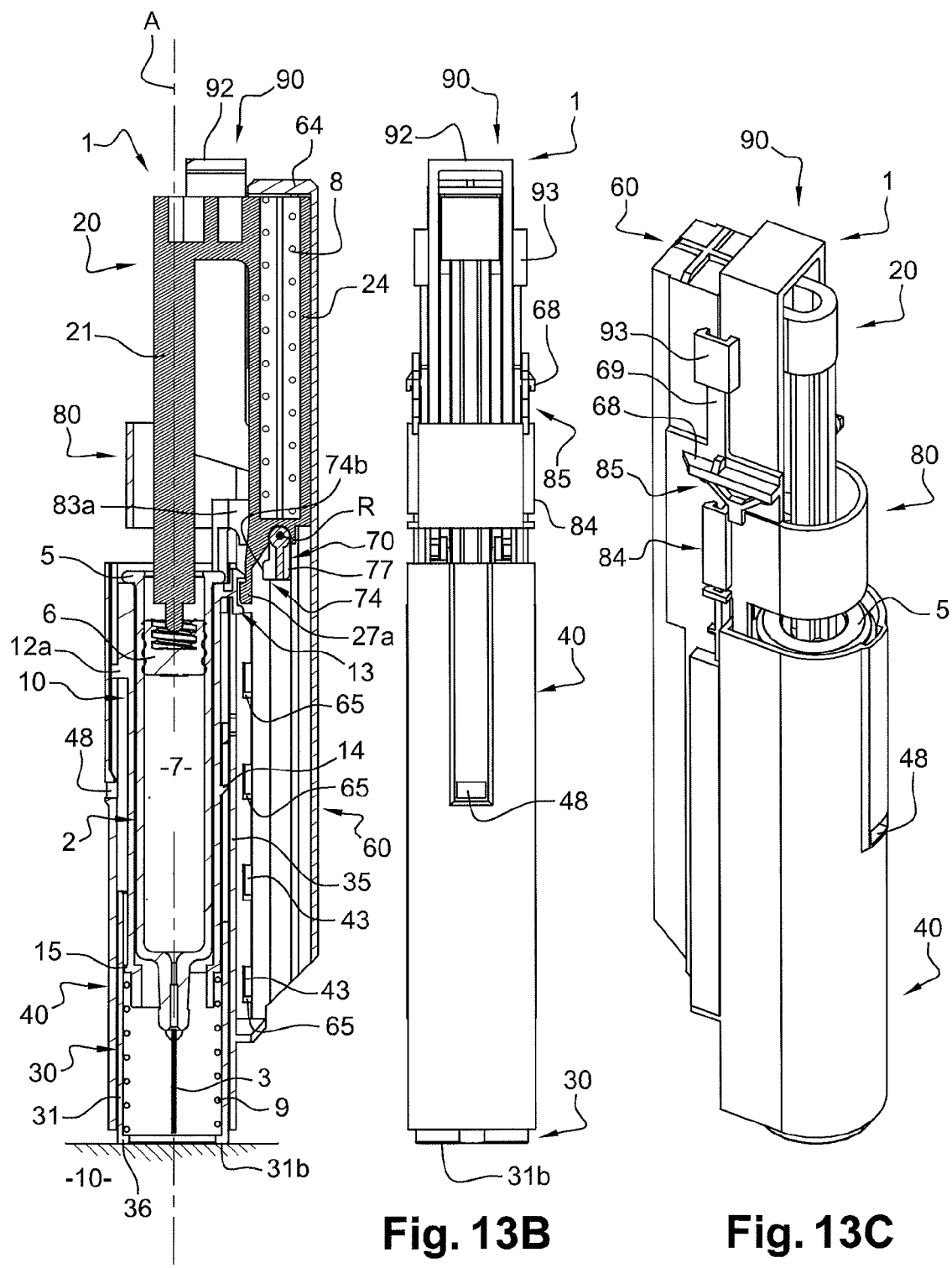
Figure 15A:
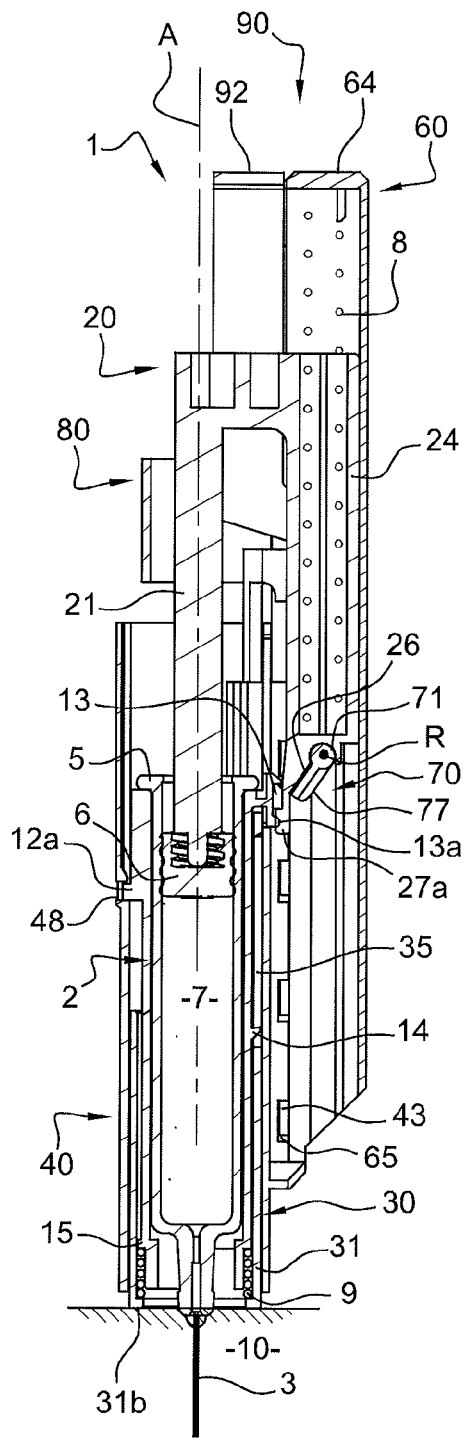
Figure 15B:
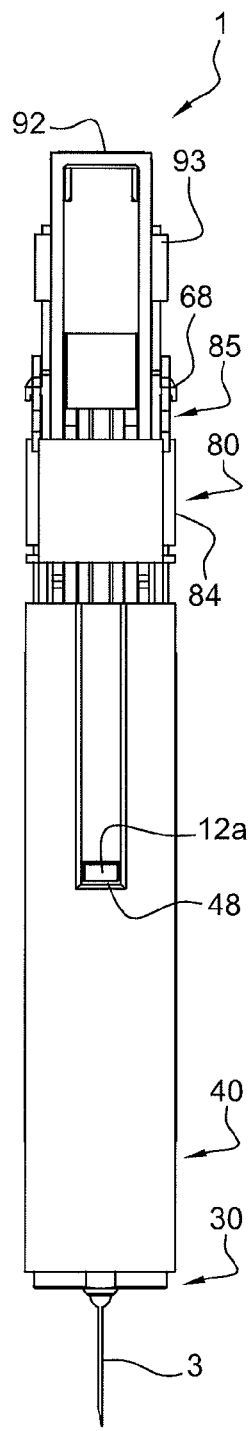
Figure 15C:
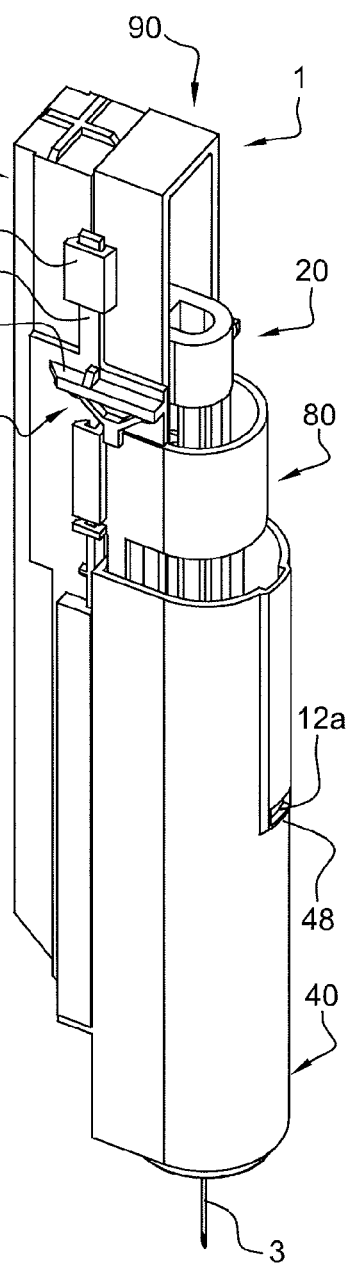
Figures 17A, 17B:
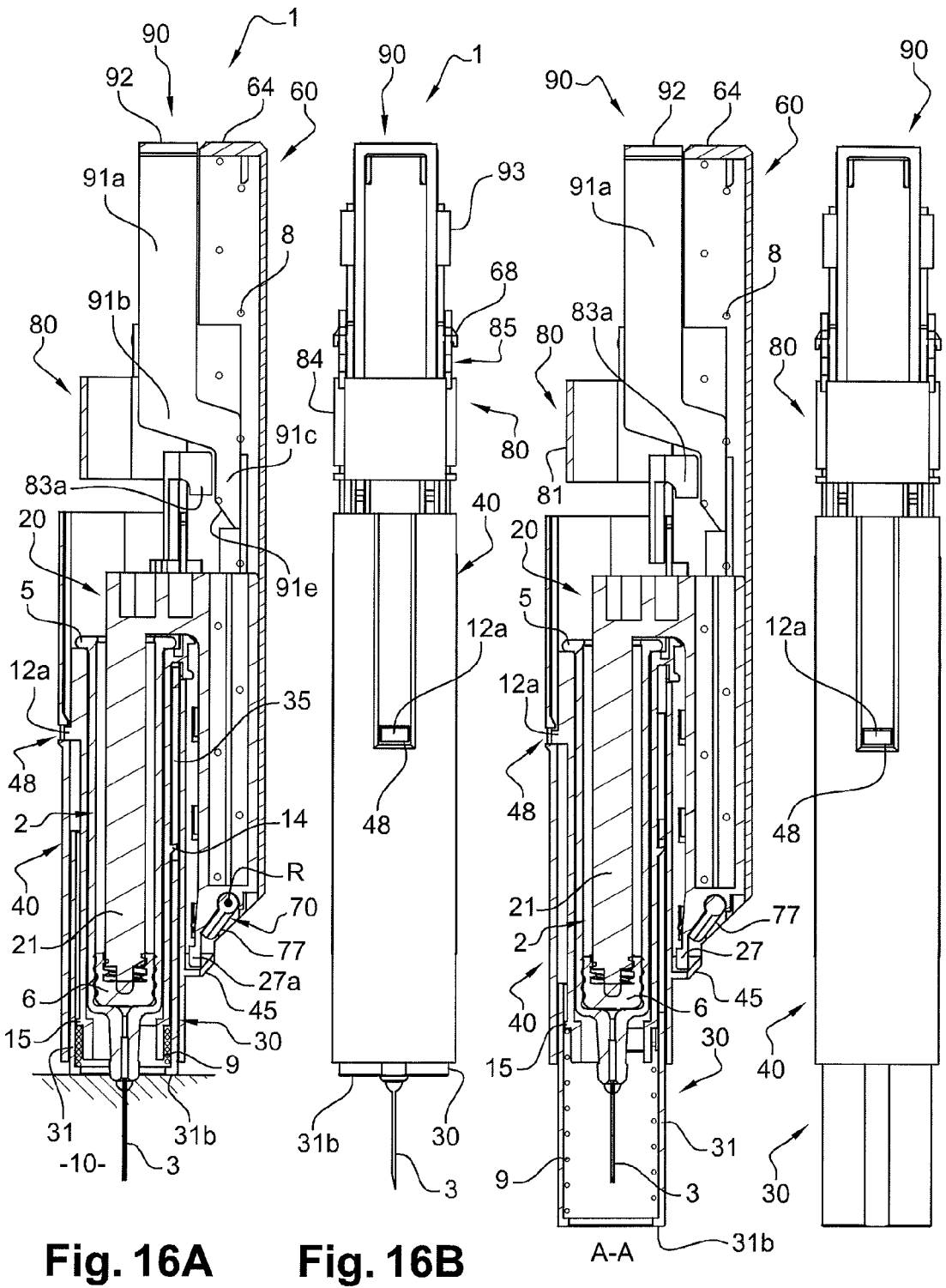
Figure 21A:
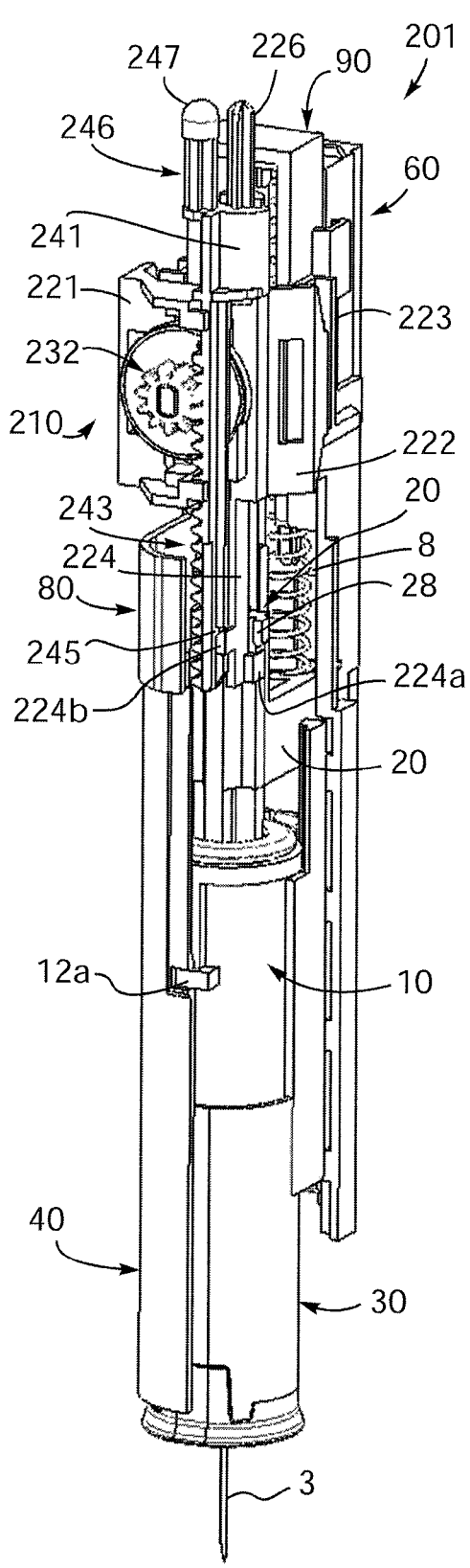
Figure 21B:
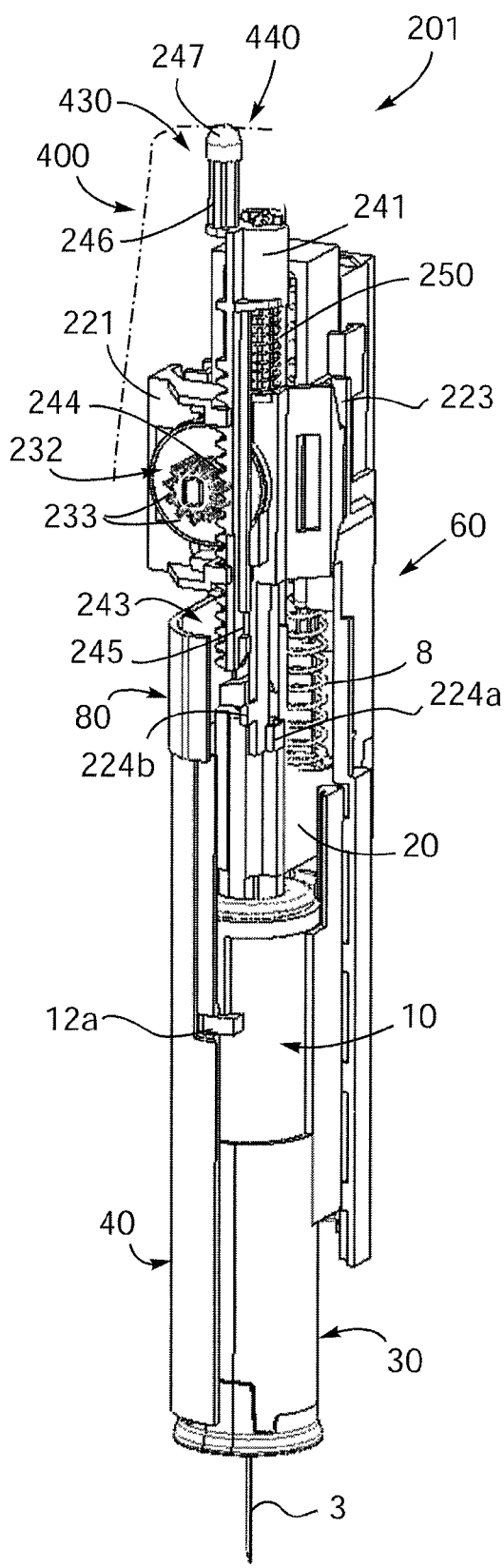
Figure 22:
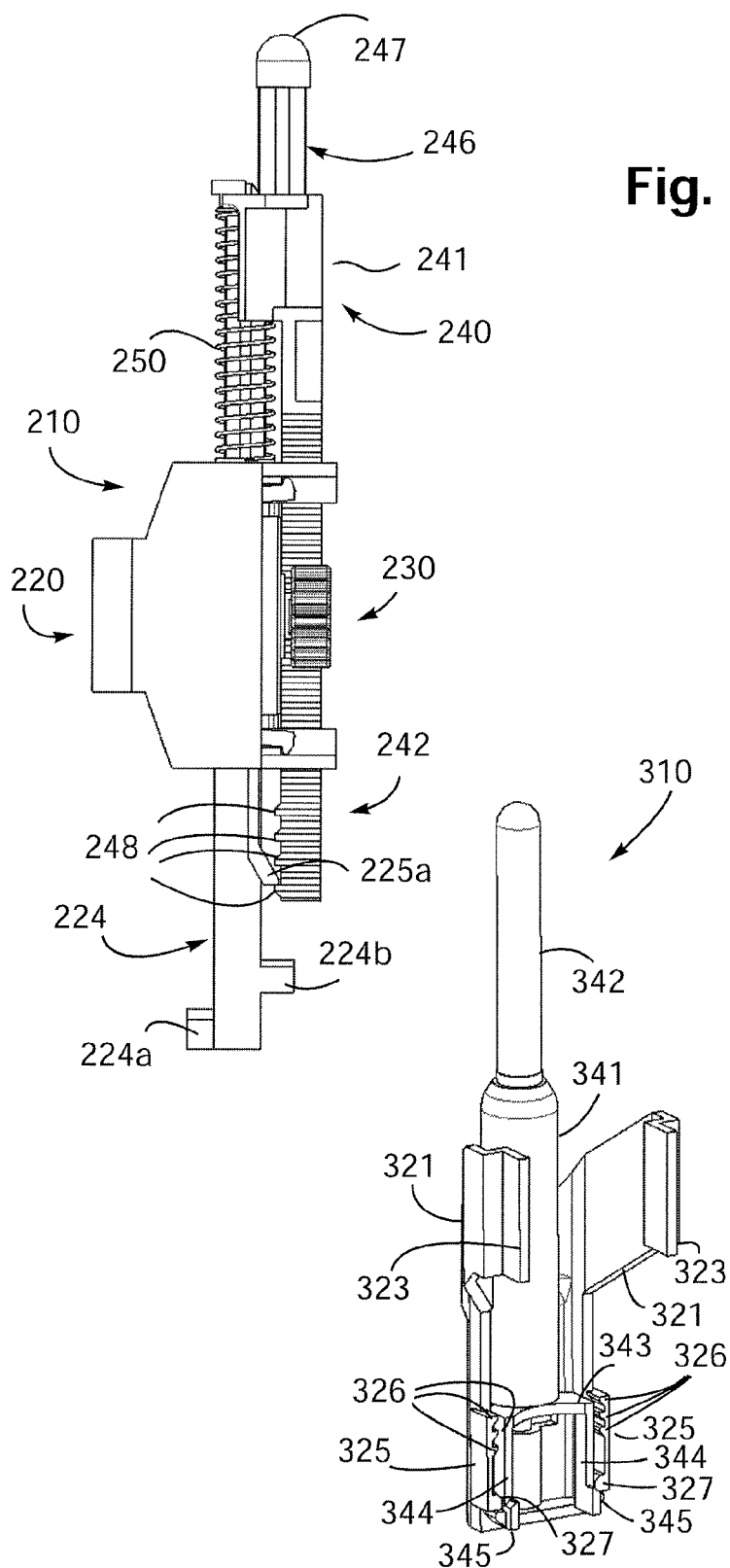
Figures 23A, 23B:
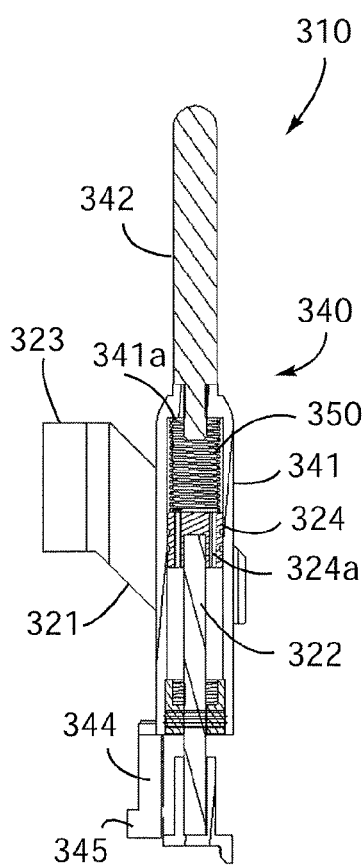
Figure 24A:
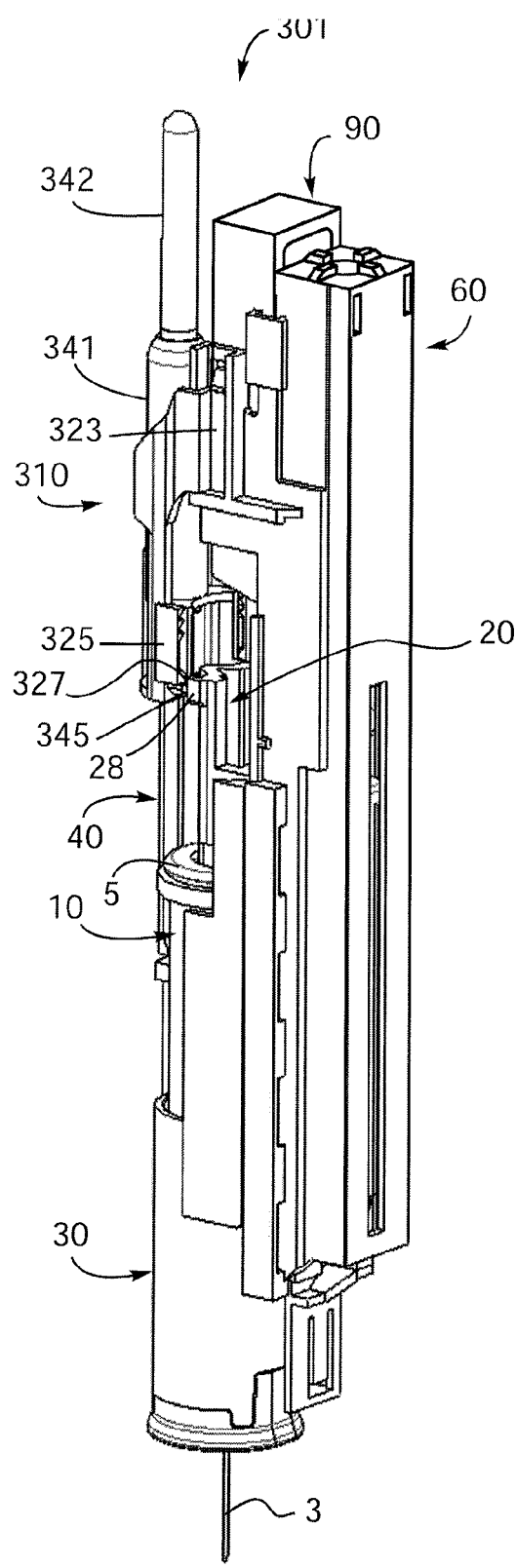
Figure 24B:
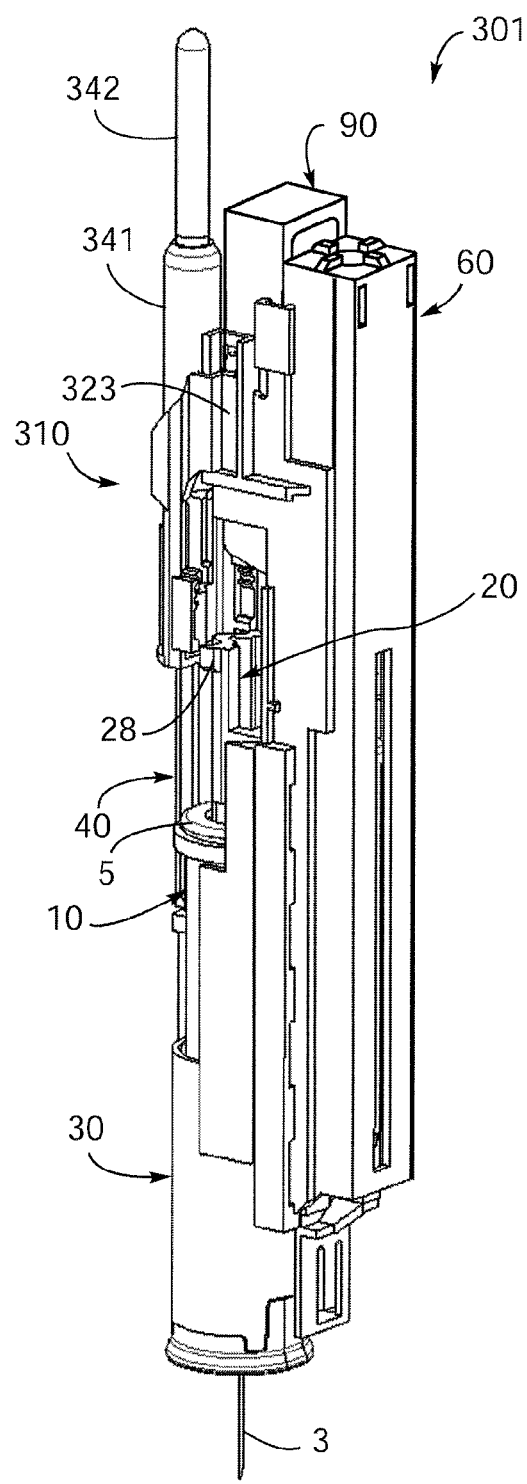
Figure 25:
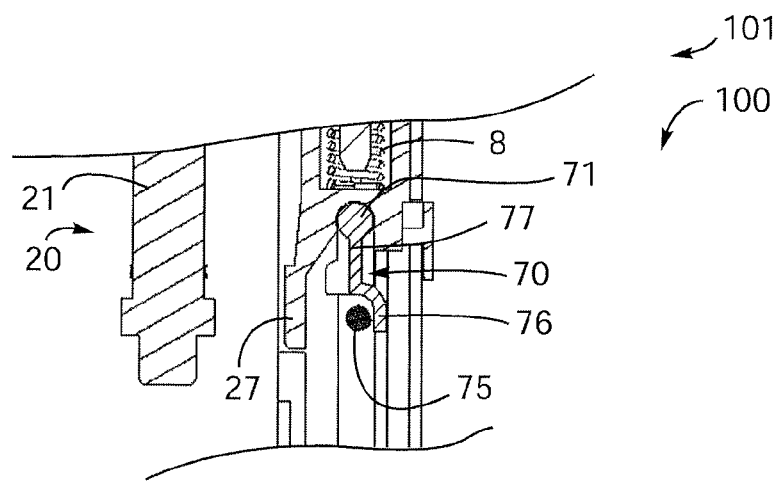
Figure 26:
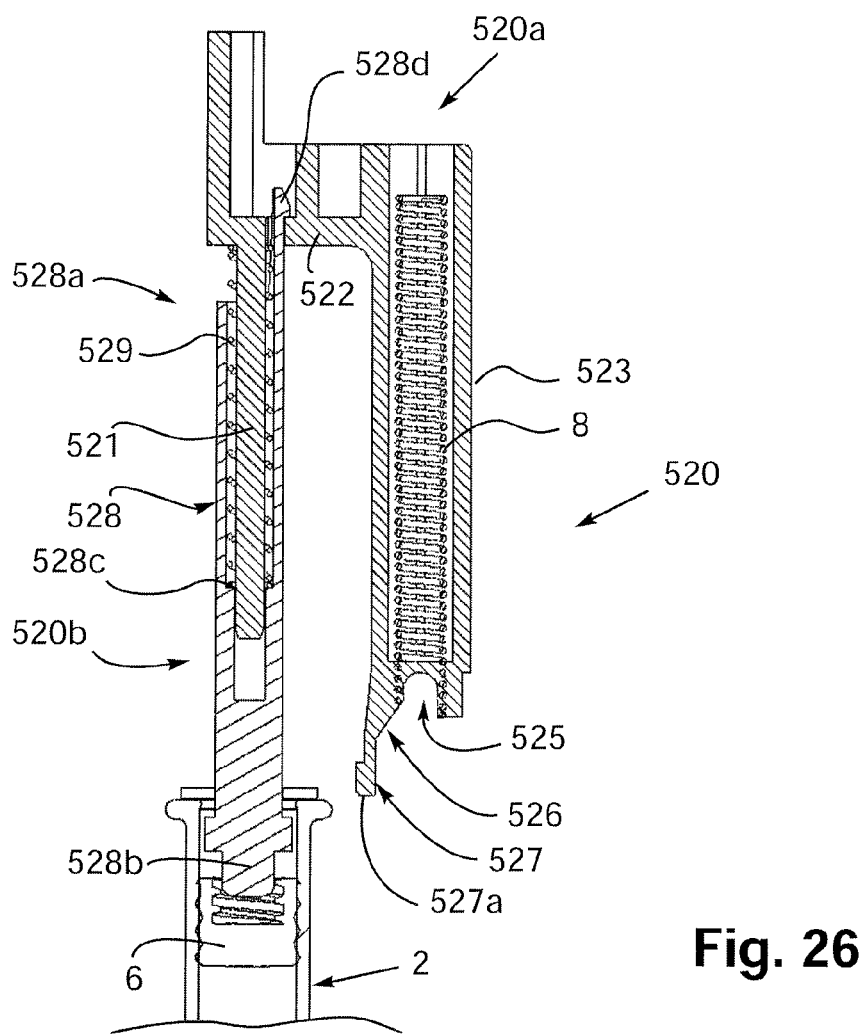

The present invention will now be described in greater detail based on the following description and the appended drawings in which:

FIGS. 1A-1C are respectively cross section view, front-view and perspective view of the device of the invention in a storage position, FIGS. 2A-C are views of the syringe holder of the device of FIG. 1A, respectively a perspective view from the top, a side view and a perspective view from the bottom, FIGS. 3A-3C are views of the plunger rod of the device of FIG. 1A, respectively a perspective view from the bottom, a perspective view from the top and a side view, FIGS. 4A-4C are views of a needle protection sleeve of the device of FIG. 1A, respectively a perspective view from the top, a front view, and a top view, FIGS. 5A-5B are views of the housing of the device of FIG. 1A, respectively a perspective view from the bottom, a perspective view from the top, FIGS. 6A-6B are views of the protection cap of the device of FIG. 1A, respectively a perspective view from the bottom and a perspective view from the top, FIGS. 6C-6E are perspective views of alternative embodiments of protection caps for the device of the invention, provided with tamper evident means, FIGS. 7A-7B are views of the support of the device of FIG. 1A, respectively a perspective view from the bottom and a perspective view from the top, FIG. 8 is a perspective view of the lever member of the device of FIG. 1A, FIGS. 9A-9C are views of the locking member of the device of FIG. 1A, respectively a perspective view from the bottom, a perspective view from the top and a side view, FIG. 10 is a perspective view of the button of the device of FIG. 1A, FIGS. 11A-11C are views of the motor part of the device of FIG. 1A, respectively a cross section view, a front view and a perspective view, FIGS. 12A and 12B are partial perspective detail views of the device of FIG. 1A in its storage position, FIGS. 13A-13C are views of the device of FIG. 1A, in a position where the deactivating means have released the locking means, and the retaining means are in their active condition, respectively a cross section view, a front view and a perspective view, FIG. 14A is a partial detail side view of the device of FIG. 1A showing the release of the locking means, FIG. 14B is a partial detail side view of the device of FIG. 1A showing the release of the retaining means, FIGS. 15A-15C are views of the device of FIG. 1A once the needle has been inserted, respectively a cross section view, a front view and a perspective view, FIGS. 16A and 16B are views of the device of FIG. 1A at the end of injection, respectively a cross section view and a front view, FIGS. 17A and 17B are views of the device of FIG. 1A after the needle protection means has reached its final position, respectively a cross section view and a front view, FIGS. 18A-E are partial perspective views of an alternative embodiment of the device of FIG. 1A, where the locking means is integrate with the needle protection means, respectively in a storage position of the device, in a position where the locking means have been released, in a position where the retaining means are being released, during the injection step, and at the end of the injection step, FIGS. 19A and 19B are respectively a front view and a back view of controlling means and temporizing means suitable for the devices of FIGS. 1A-18E, FIG. 20 is a side view of a device of the invention similar to that of FIGS. 1A-17B equipped with the controlling means and temporizing means of FIGS. 19A and 19B, FIG. 21A is a perspective partial open view of the device of FIG. 20 at the moment the temporizing means are activated, FIG. 21B is a perspective partial open view of the device of FIG. 20 at the end of the delay generated by the temporizing means, FIG. 22 is a side view of another embodiment of the temporizing means, FIG. 23A is a perspective view of an alternative embodiment of controlling means and temporizing means suitable for the devices of FIGS. 1A-18E, FIG. 23B is a cross section view of the controlling means and temporizing means of FIG. 23A, FIG. 24A is a perspective partial open view of a device of the invention with temporizing means of FIGS. 23A and 23B, when activated, FIG. 24B is a perspective partial open view of the device of FIG. 24A at the end of the delay generated by the temporizing means, FIG. 25 is a partial cross section view of the motor part of the device of FIGS. 18A-18E, before connection to the housing part, and with temporary lock, FIG. 26 is a cross section view of an alternative embodiment of a plunger rod for a device of the invention, comprising dampening means.

With reference to FIGS. 1A-1C, is shown a device 1 of the invention comprising:
- a syringe 2 comprising a needle 3 and a rubber cap 4 for the protection of the needle, a flange 5, a stopper 6, filled with a product 7,
- a syringe holder 10,
- a plunger rod 20,
- a needle protection sleeve 30,
- a housing 40,
- a protection cap 50,
- a support 60,
- a lever member 70,
- a locking member 80,
- a button 90,
- a first helical spring 8,
- a second helical spring 9

With reference to FIGS. 2-17B, the different parts of the device 1 will now be described in details.

With reference to FIGS. 2A-2C, the syringe holder 10 has the global shape of a tube. It is shaped and dimensioned so as to be able to receive the syringe 2 with the flange 5 of the syringe 2 bearing onto a proximal rim 11 of the syringe holder 10. The syringe holder 10 is provided on its outer wall with a ridge 12 extending from the proximal rim 11 in the distal direction and terminated by a peg 12a. The proximal rim 11 is further provided with a flexible hook 13 extending outwardly and proximally, this hook 13 being substantially diametrically opposed to the ridge 12 in the example shown. The hook 13 is provided with a distal outer projection 13a allowing the hook 13 to act as a jaw, as will appear from the description below. Diametrically opposed to the ridge 12, and substantially located in the middle region of the outer wall of the syringe holder 10, a radial outer peg 14 is present. The syringe holder 10 is further provided with a distal rim 15. The proximal rim 11 is further provided with two outer projections 16 projecting radially and outwardly from the proximal rim 11 and located on each side of the flexible hook 13 on the circumference of the proximal rim 11.

With reference to FIGS. 3A to 3C, the plunger rod 20 comprises a shaft 21 having a proximal end 21a and a distal end 21b. As will appear from the description below, the shaft 21 is dimensioned so as to be able to be received within the syringe 1, and its distal end 21b is free and is intended to be coupled to the stopper 6 of the syringe 1. At its proximal end 21a, the shaft 21 is provided with a bridge 22 linking the shaft 21 to a longitudinal tubular lodging 23 open at its proximal end 23a and closed at its distal end 23b. The longitudinal axis of the shaft 21 and the longitudinal axis of the longitudinal tubular lodging 23 are parallel and the plunger rod 20 has a global U-shape. On its face not facing the shaft 21, the longitudinal tubular lodging 23 is provided with a longitudinal tangential wall 24. On a distal face of a distal transversal wall, the longitudinal tubular lodging 23 is provided with a transversal semi-tubular recess 25 prolonged on one of its sides by an oblique wall 26 terminated by a distal leg 27. The distal leg 27 is provided at its distal end by a rim 27a facing the shaft 21.

With reference to FIGS. 4A-4C, the needle protection sleeve 30 is dimensioned and shaped so as to be able to receive the syringe holder 10. The needle protection sleeve 30 comprises a distal sleeve 31 having a proximal end 31a and a distal end 31b and a globally tubular shape. At its proximal end 31a, the distal sleeve 31 is provided with two lateral walls 32, parallel to each other and extending in the proximal direction. The two lateral walls 32 are linked to each other by a bridging wall 33. Each lateral wall 32 is further provided, at its corner joining the bridging wall 33, with a proximal projection 34 having a proximal face 34a. The bridging wall 33 is provided with a longitudinal window 35 having a proximal edge 35a. At its distal end 31b, the distal sleeve 31 is provided with an inner radial rim 36.

With reference to FIGS. 5A and 5B, the housing 40 has the global shape of a tube 41 open at its proximal end 41a and its distal end 41b, provided with a back wall 42 having a planar shape. The housing 40 is dimensioned and shaped so as to be able to receive the needle protection sleeve 30, the syringe holder 10 and the syringe 1. As will appear from the description below, the back wall 42 will be useful for assembling the housing 40 to the other main part of the device 1, namely the motor part 100 (see FIGS. 11A-11C). The back wall 42 is provided on the example shown with two series of outer projections 43 (four projections for one serie on the example shown) distributed longitudinally and intended to be part of the connecting means for assembling the housing 40 to the motor part 100 (FIGS. 11A-11C) of the device 1. The proximal region of the back wall 42 is provided with a window 44 open at its proximal end 44a and having a distal edge 44b. Distally spaced with respect to the outer projections 43, the back wall 42 is provided with an outer radial rim 45. Distally spaced from the outer radial rim 45, the back wall 42 is further provided with two windows 46 receiving two radially flexible tags 46a. The housing 40 is further provided on its inner wall opposite the back wall 42 with a proximal longitudinal groove 47, terminated by a window 48 (visible on FIGS. 1A and 1C).

With reference to FIGS. 6A and 6B, the protection cap 50 comprises a globally tubular distal cap 51 provided with four internal legs uniformly distributed along a central circle, extending in the proximal direction, namely two opposite short legs 52 and two opposite long legs 54. Each long leg 54 is provided at its proximal end with an inner rim 55. As will appear from the description below, the protection cap 50 is intended to be snap-fitted onto the distal end of the housing 40 for closing said sital end during storage of the device 1 up until its use.

With reference to FIGS. 6C-6E are shown alternative embodiments for the protection cap 50, where the globally tubular distal cap 51 is further provided with tamper evident means informing the user that the protection cap has already been removed at least once before having been replaced on the distal end of the housing 40. On FIG. 6C, the distal cap 51 is provided with a pair of tangential flexible legs 56, which are able to cooperate with adequate surfaces of the housing 40 so as to be compressed within said housing 40 when the device is first provided to a user, but which remain deflected once the protection cap 50 has been removed at least once from the housing 40. As a consequence, even if the protection cap 50 is replaced on the distal end of the housing 40, the deflected flexible legs 56 inform a potential second user that the protection cap 50 has already been removed and that, as a consequence and for safety reasons, the device should not be used. On FIG. 6D, the distal cap 51 is provided with a pair of opposite proximal flexible legs 57 which are also able to cooperate with adequate surfaces of the housing 40 so as to be compressed within said housing 40 before any use, but which remain deflected once the protection cap 50 has been removed at least once from the housing 40. In the same manner, on FIG. 6E, the distal cap 51 is provided with four circumferential flexible legs 58 which are also able to cooperate with adequate surfaces of the housing 40 so as to be compressed within said housing 40 before any use, but which remain deflected once the protection cap 50 has been removed at least once from the housing 40. As a consequence, for these two examples also, even if the protection cap 50 is replaced on the distal end of the housing 40, the deflected flexible legs (57, 58) inform a potential second user that the protection cap 50 has already been removed and that, as a consequence, the device should not be used.

With reference to FIGS. 7A and 7B, the support 60 has the global shape of a longitudinal cage open on one side and at the bottom. The cage therefore comprises three longitudinal walls, two lateral walls 62 and a back wall 63 bridging together the two lateral walls 62. For purposes of description of the support 60, the back is designated as being the wall bridging the two lateral walls, and the front is designated as being opposite the back. At its proximal end 60a, the support 60 comprises a top wall 64. At its distal end 60b, the support 60 is open. Each lateral wall 62 is provided in the distal region of its free side 62a with a series of four recesses 65 distributed longitudinally and intended to be part of the connecting means for assembling the support 60 (which is part of the motor part 100 of the device 1 as shown on FIGS. 11A-11C) with the housing 40 of the device 1. Slightly proximally spaced with respect to the recesses 65, the free side 62a of each lateral wall 62 is further provided with an outer longitudinal rod 66 provided with a peg 66a. Proximally spaced with respect to the outer longitudinal rod 66, each lateral wall 62 is further provided with a wall portion 67 extending in the front direction of the support 60, each wall portion 67 being provided with a transversal ridge 68 provided with a proximal peg 68a. Each lateral wall 62 is further provided with a longitudinal leg 69 extending from the wall portion 67 in the proximal direction. Each lateral wall 62 is further provided on its inner face with a longitudinal ridge 61 (only one being visible on FIGS. 7A and 7B) extending from the distal end of the lateral wall 62 and ending substantially half way through the length of said lateral wall 62, the proximal end of the longitudinal ridge 61 therefore forming an abutment surface 61a.

With reference to FIG. 8, the lever member 70 comprises a cylinder part 71 rotatable around its longitudinal axis R. The cylinder part 71 is provided with a radial projection 77 comprising two parallel radial legs 72 extending in the outward direction and bridged together via a longitudinal radial wall 73. Each radial leg 72 is provided at its free end with a peg 74 having the global shape of a parallelogram with a rounded side 74a, and a planar side 74b located opposite the rounded side 74a. As will appear from the description below, as the cylinder part 71 rotates around its longitudinal axis R, the radial projection 77 describes a circle and is capable of changing angular positions.

With reference to FIGS. 9A-9C, the locking member 80 comprises a semi-collar 81 prolonged at its free ends with two opposite side walls 82. Each side wall 82 is provided with one longitudinal leg 83 extending in the distal direction towards a distal end 83b, each longitudinal leg 83 being provided at its proximal end with an inner projection 83a extending in the direction opposite the semi-collar 81. Each side wall 82 is further provided on its outer face with a longitudinal lodging 84 extending substantially along the length of the height of the side wall 82. The lodging 84 is traversed on its whole length by a through hole 84a. In its distal region, the lodging 84 is interrupted on a slight distance thereby forming a distal recess 84b. Each side wall 82 is further provided with a flexible ring 85 having an attachment point 85a fixed to a proximal edge of the side wall 82, the flexible ring extending from this attachment point 85a in the proximal direction, the flexible ring 85 being able to adopt a flattened configuration when submitted to a distal pressure.

With reference to FIG. 10, the button 90 has a globally U shape, namely two parallel longitudinal lateral walls 91 bridged together at their proximal ends by a transversal proximal wall 92. Each lateral wall 91 has a globally rectangular proximal portion 91a, which is bent in its distal region so as to further extend as an oblique portion 91b, the oblique portion 91b being itself bent again so as to terminate as a longitudinal portion 91c, the distal end 91d of which has a pointed shape comprising a sloped surface 91e. Each lateral wall 91 is provided on the outer surface of its rectangular portion 91a with a hook 93 extending beyond an edge of the rectangular portion 91a, globally in the direction of the oblique portion 91b.

The operation of the device 1 of the invention will now be explained with reference to FIGS. 1A to 17B.

With reference to FIGS. 11A to 11C is shown what is called the motor part 100 of the device 1, namely the plunger rod 20, the support 60, the lever member 70, the locking member 80, the button 90 and the first helical spring 8 assembled altogether.

As appears from FIG. 11A, the support 60 and the plunger rod 20 are coupled together via the first helical spring 8 and the lever member 70. The first helical spring 8 is received within the longitudinal tubular lodging 23. The longitudinal tubular lodging 23 is lodged within the proximal region of the inner space of the support 60, with the longitudinal tangential wall 24 of the plunger rod 20 facing the inner face of the back wall 63 of the support 60. The distal end of the first helical spring 8 bears on the proximal face of the distal end 23b of the longitudinal tubular lodging 23, and the proximal end of the first helical spring 8 bears on the distal face of the top wall 64 of the support 60. The helical spring 8 is therefore aligned on the longitudinal axis of the longitudinal tubular lodging 23 of the plunger rod 20.

In the position of the motor part of the device as shown on FIGS. 11A-11C, the first helical spring 8 is in a first state, which is a stressed state. As such, the helical spring 8 naturally tends to separate the plunger rod 20 from the support 60. Nevertheless, the lever member 70 acts as retaining means for maintaining the first helical spring 8 in its first stressed state. Indeed, as shown on FIG. 11A, the cylinder part 71 of the lever member 70 is lodged within the semi-tubular recess 25 of the plunger rod 20 with its radial projection 77 extending through the opening of the semi-tubular recess 25. The cylinder part 71 is received in the semi-tubular recess 25 in a rotatable way: in other words, the cylinder part 71 is capable of rotating within the semi-tubular recess 25, around its longitudinal axis R (see FIG. 8), and the radial projection 77 is allowed to change angular positions in the range of angular positions allowed by the dimensions of the opening of the semi-tubular recess 25 and by the presence of the oblique wall 26 of the plunger rod 20. In the position shown on FIG. 11A, the position of the semi-tubular recess 25 on a distal face of a distal transversal wall of the longitudinal tubular lodging 23 with its opening facing the distal direction allows the radial projection 77 of the rotatable cylinder part 71 to extend in the distal direction. The pegs 74 are in distal abutment against the abutment surfaces 61a of the longitudinal ridges 61 of the lateral walls 62 of the support 60.

In addition, as shown on FIGS. 11A-11C, the lever member 70 is positioned so as to have its rotatable cylinder part 71 included in a plane that is transversal with respect to the longitudinal axis of the longitudinal tubular lodging 23 of the plunger rod 20. In this position of the motor part 100, the lever member 70 is prevented from rotating around the longitudinal axis R of its cylinder part 71 by means of the inner projections 83a of the locking member 80 coming in abutment against the planar sides 74b of the pegs 74. As appears from FIG. 11C, the locking member 80 is slidingly mounted on the support 60 by means of its longitudinal lodgings 84 receiving the outer longitudinal rods 66 of the support 60. The distal ends of the longitudinal lodgings 84 being in abutment on the peg 66a (see FIG. 7B) of the longitudinal rod 66, the locking member 80 is not slidable with respect to the support 60 in the distal direction. Nevertheless, the locking member 80 is slidable with respect to the support 60 in the proximal direction.

As shown also on FIG. 11C, in this assembled position of the motor part 100 of the device of the invention, the semi-collar 81 of the locking member 80 surrounds the distal region of the shaft 21 of the plunger rod 20 and the flexible rings 85 of the locking member 80 are distally spaced from the transversal ridge 68 of the wall portion 67 of the lateral walls 62 of the support 60.

As further shown on FIGS. 11A-11C, the motor part 100 of the device further comprises the button 90 which is slidingly mounted on the support 60. As more clearly shown on FIG. 11C, the button 90 is mounted on the support 60 by means of the longitudinal legs 69 of the lateral walls 62 of the support 60 being received within the hook 93 of the button 90 and being allowed to slide therein.

As shown on FIGS. 11A-11C, the motor part 100 is an autonomous part of the device 1 of FIG. 1A, that may be transported and/or handled on its own. This motor part 100 is intended to be connected to the housing part of the device, said housing part comprising the housing 40 containing the prefilled syringe 2, as will appear from the description below. In this view, the motor part 100 comprises means for connecting the support 60 to the housing 40, under the form of the recesses 65.

With reference to FIGS. 1A-1C, the motor part 100 of FIGS. 11A-11C has been connected to the housing part for forming the device 1 of the invention. The motor part 100 is connected to the housing 40 of the housing part by means of the projections 43 of the housing 40 being snap-fitted within the corresponding recesses 65 of the support 60. As such, all the elements of the motor part which were previously described as being coupled the support 60 are therefore now coupled to the housing 40 itself, via said support. In the same way, the elements of the motor part which were previously described as being slidingly mounted with respect to the support 60, such as the button 90, are now slidingly mounted with respect to the housing 40.

As appears from comparison between FIG. 11C and FIG. 1C, the connection of the housing part to the motor part 100 has caused the locking member 80 to be slightly moved in the proximal direction with respect to the support 60. As a consequence, the proximal end of each flexible ring 85 now comes in contact with the distal face of the transversal ridge 68, yet without stressing said flexible rings 85. The role of the flexible rings 85 will be described later in the description.

With reference to FIG. 1A, although the locking member 80 has moved proximally, the inner projections 83a of the locking member 80 still come in abutment against the planar sides 74b of the pegs 74, thereby preventing the lever member 70 to rotate as explained above.

With reference to FIG. 1A, the arrangement between the various elements received within the housing 40, and therefore forming the housing part of the device 1, will now be described. The housing 40 has a longitudinal axis A, aligned on the proximal-distal direction.

A first element contained in the housing 40 is a container, having the form of a syringe 2 in the example shown, aligned on the longitudinal axis A. The syringe 2 has a global tubular shape and is substantially closed at its distal end by a needle 3 for the exit of the product to be injected. As shown on FIG. 1A, the syringe 2 is prefilled with the product 7 to be injected and is closed at its proximal end by a stopper 6. As will appear in the following description, the stopper 6 is capable of moving within the syringe 2 under distal pressure and is intended to cooperate with the distal end of the shaft 21 of the plunger rod 20 in order to realize injection of the product 7. The syringe 2 is further provided at its proximal end with an outer flange 5. In the storage position of the device 1 as shown on FIG. 1A, the syringe 2 is further provided at its distal end with a rubber cap 4 surrounding the needle 3 so as to protect it. In an embodiment not shown, the rubber cap may also comprise a rigid part.

The thus prefilled syringe 2 is received within the syringe holder 10 by means of the distal face of its outer flange 5 bearing onto the proximal rim 11 (see FIG. 2A) of the syringe holder 10. The syringe holder 10 is also aligned on longitudinal axis A and the syringe 2 is therefore blocked in distal translation with respect to the syringe holder 10. In addition, the syringe is further blocked in proximal translation with respect to the syringe holder 10 by means of friction force existing between the syringe 2 and the syringe holder 10; As a consequence, all elements herein described as being coupled to the syringe holder 10 are therefore also coupled to the syringe 2.

In the storage position of the device 1 as shown on FIGS. 1A-1C, the distal region of the syringe holder 10 is received in the needle protection sleeve 30. The needle protection sleeve 30 is aligned on longitudinal axis A. The syringe holder 10 is coupled to the needle protection sleeve 30 first by means of a second helical spring 9, which is in a first stressed state, so that the distal end of second helical spring 9 bears on the proximal face of the inner radial rim 36 of the distal sleeve 31 of the needle protection sleeve 30, and the proximal end of the second helical spring 9 bears on the distal face of the distal rim 15 of the syringe holder 10. The second helical spring 9 being in a first stressed state, it tends to separate the syringe holder 10 from the needle protection sleeve 30: as such, the syringe holder 10 and the needle protection sleeve 30 are further coupled together by means of radial outer peg 14 of the syringe holder 10 being in proximal abutment against the proximal edge 35a of longitudinal window 35 of the bridging wall 33 of the needle protection sleeve 30. As such, the radial outer peg 14 and the proximal edge 35a of longitudinal window 35 act as means for maintaining the second helical spring 9 in its first stressed state.

As shown on FIG. 1A, the syringe holder 10 and the needle protection sleeve 30 are further received within the housing 40, the syringe holder 10 being slidingly mounted on the housing 40 by means of the peg 12a of its ridge 12 being engaged in the proximal longitudinal groove 47 of the housing 40. In this position, the outer projections 16 of the syringe holder 10 (see FIG. 2A) enter the window 44 of the housing 40 by its open proximal end 44a (see FIG. 5B), the outer projections 16 coming in distal abutment against the distal edge 44b of the window 44 of the housing 40.

In the storage position of the device 1 as shown on FIG. 1A, the syringe holder 10 is further connected to the motor part 100 of the device 1 by means of the rim 27a of the distal leg 27 of the plunger rod 20 being engaged in flexible hook 13 of the syringe holder 10.

The device 1 of FIG. 1A further comprises a protection cap 50 for protecting the distal end of the device 1, in particular the needle 3. The protection cap 50 is mounted on the housing 40 by connection means (not shown) present on the distal cap 51. The long legs 54 and the inner rim 55 are means for removing the rubber cap 4 from the distal end of the syringe 2. The short legs 52 are received within the second helical spring 9, the proximal end of said legs facing the distal end of the syringe holder 10 to avoid any distal displacement of the needle protection sleeve 30 when the filled syringe is loaded into the housing part of the device.

Regarding the motor part 100, apart from the locking member 80 which has been slightly moved proximally by connection to the housing 40 as described above, the arrangement and positions of its various elements in FIGS. 1A-1C are the same than the ones already described FIGS. 11A-11C and are not repeated here again.

In particular, in the position of FIGS. 1A-1C, the lever member 70 is positioned so as to have its rotatable cylinder part 71 included in a plane transversal to the longitudinal axis A of the syringe 2. The radial projection 77 has an angular position such that said radial projection 77 extends distally from the cylinder part 71.

Moreover, in this position of FIGS. 1A-1C, the shaft 21 of the plunger rod 20, coupled to the stopper 6 via its distal end, is aligned on the longitudinal axis A of the syringe. As a consequence, the helical spring 8, which is lodged in the tubular lodging 23 of the plunger rod 20, is aligned on the longitudinal axis of the tubular lodging 23, which is parallel but separate from the longitudinal axis A. As will appear later in the description, this lateral position of the helical spring 8 with respect to the longitudinal axis A will allow the helical spring 8 to produce a distal force parallel to the longitudinal axis A when said helical spring 8 is freed. In the position of the device 1 shown on FIGS. 1A-1C, the housing 40 is fixed with respect to the support 60.

Although the housing 40, and the various elements it contains, namely the syringe 2, the syringe holder 10, the needle protection sleeve 30, the rubber cap 4, the protection cap 50, has been described above in a position where it is connected to the motor part 100 of the device 1, such housing 40 and its elements form an autonomous part of the device 1 that may be transported and/or handled on its own.

The device 1 of the invention has therefore advantages for the pharmaceutical companies, which may fill the syringe 2 on a first site, and assemble the syringe 2 in the housing 40 on this first site, while the motor part 100 of the device 1 may be assembled on a second site. The motor part 100 and the housing 40 may then be connected to each other so as to obtain the device 1.

The device 1 of the invention is provided to the user in the configuration shown on FIGS. 1A-1C, preferably surrounded by an outer shell 400, as shown on FIG. 20. The user is usually a patient that will complete the injection on his own. When the user is ready, he grasps the device 1 of FIGS. 1A-1C and he removes the protection cap 50. During the step of removal of the protection cap 50, thanks to the syringe holder 10 being firmly connected to the motor part 100 of the device 1 by means of the rim 27a of the distal leg 27 of the plunger rod 20 being engaged in flexible hook 13 of the syringe holder 10, the syringe 2 remains in the same position and is not submitted to back and forth movements in the distal and proximal directions.

Once the cap 50 is removed, the device 1 may not be triggered as long as the device 1 is not applied in a proper way on the skin of the patient. Indeed, the removal of the cap 50 has not changed the relationship between the support 60 and the plunger rod 20, and in particular between the lever member 70 and the locking member 80.

FIG. 12A is a partial detail perspective view of the relationship between the locking member 80 and the lever member 70 in the position of the device 1 where the protection cap 50 has been removed but the device 1 has not yet been applied on the skin of the patient. For clarity's sake, the support 60 is not shown on FIG. 12A: nevertheless, it must be born in mind that the distal end of the pegs 74 are in abutment on the abutment surface 61a of the longitudinal ridge 61 of the support 60 (see FIG. 11A). With reference to FIG. 12A, in this position of the device 1, the cylinder part 71 of the lever member 70 is not allowed to rotate along its longitudinal axis R because of the planar sides 74b of the pegs 74 being in abutment against the inner projections 83a of the locking member 80.

FIG. 12B is a view similar to FIG. 12A, on which the representation of the distal end 91d of the longitudinal portion 91c of the button 90 has been added. It appears clearly from this FIG. 12B that, if the user pushes distally on the transversal wall 92 of the button 90 (see FIGS. 10 and 1A), the distal end 91d of the longitudinal portion 91c of the button will move distally but will have no action on the lever member 70. In particular, the sloped surface 91e of the distal end 91d of the button may come in contact with the rounded side 74a of the peg 74 of the lever member 70, but nothing will happen, as the lever member 70 is not allowed to rotate, as explained above. The lever member 70 therefore acts as retaining means for maintaining the first helical spring 8 in its first stressed state, and the lever member 70 is in a passive condition, as activation of the button 90 has no effect on the lever member 70 and therefore does not trigger the injection. The locking member 80 acts as locking means for preventing the triggering means (button 90 and its sloped surface 91e) from moving the lever member from its passive condition to its active condition.

With reference to FIGS. 12A and 12B, one can see that, in this passive condition of the lever member 70, the proximal face 34a of each proximal projection 34 of the needle protection sleeve 30 (partially shown) faces directly the distal end 83b of a longitudinal leg 83 of the locking member 80.

As a consequence, for releasing the locking member 80 and allowing the lever member 70 to be able to go from its passive condition to an active condition, in which the insertion of the needle may be triggered, the user needs to apply the device 1 on his skin or on the skin of the patient via the distal end 31b of the distal sleeve 31 of the needle protection sleeve 30 as shown on FIG. 13A, and then push distally on the housing 40. Because of the relationship described above between the housing 40 and the needle protection sleeve 30, this movement causes the needle protection sleeve 30 to move proximally with respect to the housing 40, and therefore with respect to the support 60, which is fixed with respect to the housing 40. While the needle protection sleeve 30 moves proximally with respect to the support 60, the proximal faces 34a of its proximal projections 34 push proximally onto the distal ends 83b of the locking member 80, since said distal ends 83b face the proximal faces 34a of the proximal projections 34 of the needle protection sleeve 30, as shown on FIGS. 12A and 12B.

As a consequence, and with reference to FIG. 14A which schematically shows the inner projection 83a of the locking member 80, the peg 74 of the lever member 70 and the distal end 91d of the button 90, the inner projection 83a of the locking member 80 is moved proximally with respect to the peg 74 of the lever member 70, said inner projection 83a no more facing the planar side 74b of the peg 74 of the lever member 70. The locking member 80 has therefore been released and distal movement of the button 90 is now capable of rotating the cylinder part 71 of the lever member 70, as will appear later from description of FIG. 14B. During this step, the proximal faces 34a of the proximal projections 34 of the needle protection sleeve 30 form deactivating means of the locking member 80, acting as locking means for preventing the triggering means from moving the retaining means, namely the lever member 70, from its passive condition to its active condition.

As shown on FIG. 13A, the inner projection 83a of the locking member 80 no more faces the planar side 74b of the peg 74 of the lever member 70. With reference to FIG. 13C, one can see that the proximal movement of the locking member 80 with respect to the support 60, allowed as the locking member 80 is slidingly mounted on the support 60, has caused the flexible rings 85 to come in abutment against the distal face of the transversal ridges 68 of the support 60, thereby reaching their flattened condition corresponding to their stressed condition. The flexible rings 85 therefore allow the deactivating means, namely the needle protection sleeve 30, to come back to its storage position in case the user is not satisfied by the location where he has applied the device 1 on the skin in the first place and decides to remove the device 1 from the skin in order to apply it at another location before triggering injection. When the user removes the device 1 from the first location, the flexible rings 85 come back to their rest state automatically and cause the distal movement of the locking member 80, thereby locking again the triggering means. The flexible rings 85 therefore act as storage elastic return means for urging the needle protection sleeve 30 back in its storage position, in the absence of any pressure applied on said housing 40 or needle protection sleeve 30.

The device 1 of the invention is therefore safe, as the user is allowed to give more than just one try in order to choose the location on the skin where he wishes to trigger the injection.

Once the user is satisfied with the location on the skin where he has applied the device 1, and once the locking means are released, as explained above, the user pushes distally on the transversal proximal wall 92 of the button 90. The button 90 being slidingly mounted onto the support 60, the distal end 91d of the button moves distally with respect to the lever member 70. This movement causes the sloped surface 91e of the distal end 91d of the button 90 to come in contact with the rounded side 74a of the peg 74 of the lever member 70, as shown on FIG. 14B, causing the rotation of the cylinder part 71 (see FIG. 8) of the lever member 70 around its longitudinal axis R. Only little force is required from the user for pushing the sloped surface 91e as the user may benefit from natural gravitational force for completing this step, the button 90 being slidingly mounted onto the support 60 along a direction parallel to said longitudinal axis A.

The radial projection 77 moves from its first angular position (extending in the distal direction) to its second angular position, in which it is parallel to the oblique wall 26 (see FIG. 15A) acting as an abutment surface for maintaining the radial projection 77 in this second angular position.

As a consequence of the radial projection 77 reaching its second angular position, the distal face of the peg 74 escapes the abutment surface 61a of the longitudinal ridge 61 of the lateral wall 62 of the support 60. While pressing distally onto the transversal wall 92 of the button, the only resistance the user has to overcome is the angular displacement of the radial projection 77: such an angular displacement requires only very little force to be completed. The user needs not apply a high force on the button 90 in order to complete this step. The activation of the triggering means and the initiation of the insertion step of the needle is therefore very easy and simple: the user has no anxiety to face as the step proceeds very softly and smoothly.

The moving of the lever member 70 from its passive condition to its active condition frees the first helical spring 8 which expands, as it automatically tries to reach a less stressed state than its first state. The button 90 therefore acts as triggering means for releasing the retaining means, namely the lever member 70. While expanding, the helical spring 8 produces a distal force along the axis of the longitudinal tubular lodging 23, said axis being parallel to the longitudinal axis A. The plunger rod 20, thanks to its bridge 22 and its shaft 21, is shaped and dimensioned so as to transmit this distal force to the syringe 2.

Because of the gliding resistance of the stopper 6, which is reinforced by the fact that the rim 27a of the distal leg 27 of the plunger rod 20 is engaged in the flexible hook 13 of the syringe holder 10, the stopper 6 does not move with respect to the syringe 2, but the plunger rod 20, the syringe holder 10 and the syringe 2 are all driven in the distal direction, thereby realizing the insertion of the needle 3 into the injection site 10, as shown on FIG. 15A. The rim 27a of the distal leg 27 of the plunger rod 20 and the flexible hook 13 of the syringe holder 10 therefore form maintaining means for maintaining the syringe 2 fixed with respect to the plunger rod 20 when the first helical spring 8 goes from its first state to its second state. During this step, the first helical spring 8 therefore acts as biasing means for moving the syringe 2 from its first position to its second position, said second position being an insertion position (needle inserted into the injection site).

In this position of the device 1 where the needle 3 is inserted in the injection site 10, and the distal end of the syringe 2 comes in abutment with the skin of the patient, as shown on FIG. 15A, the peg 12a of the syringe holder 10 has reached the window 48 of the proximal longitudinal groove 47 of the housing 40 in which it has become engaged. As a consequence, the syringe holder 10 is now no more slidable with respect to the housing 40. The peg 12a and the window 48 therefore act as fixing means for maintaining the syringe 2 in its second position with respect to the housing 40. Moreover, the distal movement of the syringe holder 10 with respect to the needle protection sleeve 30 has caused the second helical spring 9 to reach a second state, in which it is more stressed than in its first state.

As a consequence, from this step on, the syringe holder 10 will remain fixed with respect to the housing 40, and the removal of the device 1 from the skin of the patient will automatically cause the expansion of the second helical spring 9 and therefore the movement of the needle protection sleeve 30 to its final position, in which it surrounds the needle 3 (see FIG. 17A). The device 1 of the invention is therefore very safe and requires no additional effort from the user for triggering the protection of the needle 3 as soon as the insertion step is completed, regardless from the fact that the injection step has started or not.

Once the needle 3 is inserted, the first helical spring 8 continues to expand towards a third state, less stressed than its second state. As is shown on FIG. 15A, the distal end of the syringe 2 being now in abutment against the skin of the patient, the syringe 2 cannot be moved further on in the proximal direction, and the force of the helical spring 8 now causes the rim 27a of the distal leg 27 of the plunger rod 20 to escape the flexible hook 13 of the syringe holder 10 by overcoming the distal outer projection 13a of this hook 13, thereby causing the distal movement of the stopper 6 within the syringe 2. The injection therefore takes place and the product 7 is expelled into the injection site 10 through the needle 3 until the stopper 6 reaches the distal end of the syringe 2, as shown on FIG. 16A. In this position of end of injection, the rim 27a of the distal leg 27 of the plunger rod 20 comes close to the outer radial rim 45 of the housing 40.

During this step, the first helical spring 8 acts as urging means for distally moving the stopper 6 once the syringe 2 has reached its second position, and therefore realize injection of the product 7. As such, in the example shown on these figures, the biasing means and the urging means are under the form or a single helical spring, namely the first helical spring 8, going from a first state to a second state, and then from said second state to a third state, said third state being less stressed than said second state, said second state being less stressed than said first state.

Whatever the necessary intrinsic force of the helical spring 8 for completing both the insertion step and the injection step, the effort required from the user at the beginning of the process for initiating the insertion step remains low due to the arrangement of the lever member 70.

In embodiments not shown, the biasing means and the urging means could be under the form of two different helical springs. In embodiments, these two different helical springs could be concentric.

The user then removes the device 1 from the injection site, and, as already explained above, the second helical spring 9 naturally expands from its second state to a rest state and causes the needle protection sleeve 30 to move distally with respect to the syringe 2 and to cover the needle 3, as shown on FIG. 17A. The needle protection sleeve 30 therefore acts as needle protection means movable with respect to said housing 40 when the syringe 2 is fixed in its second position with respect to said housing 40 between an insertion position, in which the distal tip of the needle extends beyond the distal end of the needle protection means, and a final position, in which the distal tip of the needle does not extend beyond the distal end of the needle protection means and is surrounded by the needle protection means. During this step, the second helical spring 9 acts as elastic return means for automatically moving said needle protection means (needle protection sleeve 30) from its insertion position to its final position, upon removal of the device 1 from the injection site 10 by the user.

FIGS. 18A-18E are partial views showing only the needle protection sleeve, the lever member and the button of a device 101 which is an alternative embodiment of the device 1 of FIGS. 1A-17B, in which the locking means is integrate with the needle protection sleeve. The other parts of the device 101 being identical to that of the device 1 of FIGS. 1A-17B, for sake of clarity, they are not shown again on the Figures. On these Figures, the lever member is identical to that of the device 1 of FIGS. 1A-17B and the same references have been maintained.

With reference to FIGS. 18A-18E, the needle protection sleeve 130 is dimensioned and shaped so as to be able to receive a syringe holder like in FIGS. 1A-17B. The needle protection sleeve 130 comprises a distal sleeve 131 having a proximal end and a distal end and a globally tubular shape. At its proximal end, the distal sleeve 131 is provided with two lateral walls 132, parallel to each other and extending in the proximal direction. The two lateral walls 132 are linked to each other by a bridging wall 133 identical to the bridging wall 33 of the device of FIGS. 1A-17B. Each lateral wall 132 is further provided, at its corner joining the bridging wall 133, with a proximal projection 134 having a proximal face 134a. Each proximal face 134a is further provided with a proximal leg 137. Each proximal leg 137 is provided at its proximal end with a transversal wall 138 extending in the backward direction and terminated by a planar wall 139. At its distal end, the distal sleeve 131 is provided with an inner radial rim (not visible on the Figures) identical to inner radial rim 36 of FIGS. 1A-17B.

With reference to FIGS. 18A-18E, the button 190 comprises two parallel longitudinal lateral walls 191 bridged together at their proximal ends by a transversal proximal wall 192. Each lateral wall 191 has a globally longitudinal portion 191c, the distal end 191d of which has a pointed shape comprising a sloped surface 191e.

The device 101 has no part corresponding to the locking member referenced 80 of the device 1 of FIGS. 1A-17B. In device 101, the locking means is the surface corresponding to the planar wall 139 of the transversal wall 138 of the needle protection sleeve 130.

With reference to FIG. 18A, the device 101 is in its storage position. In this position, the lever member 70 is positioned so as to have its rotatable cylinder part 71 included in a plane transversal to the longitudinal axis A of the syringe (not shown). The radial projection 77 has an angular position such that said radial projection 77 extends distally from the cylinder part 71.

The planar wall 139 is in abutment against the peg 74, therefore preventing the lever member 70 to rotate, even if a user pushes distally on the button 190 thereby causing distal movement of the distal end 191d of the button 190. The lever member 70 is in its passive condition and the planar wall 139 acts as locking means preventing the triggering means (button 190) from moving the lever member 70 from its passive condition to its active condition.

With reference to FIG. 18B, the device 101 has been applied on the skin of the patient and the user has pushed distally on the housing (not shown) in the same manner as that described in FIGS. 1A-17B for device 1. As a consequence, the needle protection sleeve 130 has moved proximally with respect to the lever member 70, and the planar wall 139 now faces the peg 74 no more. The locking means (planar wall 139) have been released by the needle protection means 30 acting as deactivating means.

With reference to FIG. 18C, the user has pushed distally on the transversal wall 192 of button 190, thereby causing distal movement of the distal end 191d of the button 190 with respect to the lever member 70. The sloped surface 191e of the button 190 comes in abutment on the rounded side of peg 74, causing the rotation of the lever member 70. The radial projection 77 of the lever member 70 moves from its first angular position to its second angular position and escapes the support (not shown), freeing the first helical spring (not shown) in the same manner as that described for the device 1 of FIGS. 1A-17B.

Like in the embodiment of FIGS. 1A-17B, while pressing distally onto the button 190, the only resistance the user has to overcome is the angular displacement of the radial projection 77: such an angular displacement requires only very little force to be completed. The user needs not apply a high force on the button 190 in order to complete this step. The activation of the triggering means and the initiation of the insertion step of the needle is therefore very easy and simple: the user has no anxiety to face as the step proceeds very softly and smoothly.

With reference to FIG. 18D, the device 101 is shown in its position where the needle (not shown) has been inserted. With reference to FIG. 18E, the device 101 is shown in its position where the needle protection sleeve 130 is in its final position.

With reference to FIG. 25 is shown a partial view of the motor part 100 of the device 101 of FIGS. 18A-18E, before connection to the housing part, and with temporary lock, under the shape of an axle 75 fixed with respect to support 60, facing the lever member 70 for preventing said lever member 70 to rotate. In this view, the lever member 70 is further provided with a distal leg 76 designed for facing axle 75. Once the motor part 100 is connected to said housing part, the axle 75 is removed from said motor part 100 and then replaced by the surface 139 of needle protection sleeve 130.

With reference to FIGS. 19A and 19B is shown a controlling means and temporizing means assembly 210 suitable for devices 1 and 101 of FIGS. 1A-18E. The controlling means and temporizing means assembly 210 of FIGS. 19A and 19B comprises a holder 220 bearing a damping gear wheel 230 coupled with a sensitive indicator 240 via a helical spring 250.

With reference to FIGS. 19A and 19B, the holder 220 comprises a back wall 221 connecting together two lateral walls 222. The back wall 221 is intended to receive the damping gear wheel 230: the damping gear wheel 230 is fixed to the back wall 221 in a classical way. Each lateral wall 222 is provided at its free edge 222a with a longitudinal hook 223: as will appear from the description below, these hooks 223 are intended to maintain the controlling means and temporizing means assembly 210 fixed to the support 60 of the device of FIGS. 1A-18E. The holder 220 is provided with a first longitudinal leg 224 extending from the back wall 221 in the distal direction and provided at its distal end with a side peg 224a. Slightly proximally spaced from the side peg 224a, the longitudinal leg 224 is further provided with a front peg 224b. The back wall 221 is further provided with a second longitudinal leg 225 extending in the distal direction and globally parallel to the first longitudinal leg 224, the second longitudinal leg 225 being shorter than the first longitudinal leg 224. The second longitudinal leg 225 is provided at its distal end with a front rim 225a. Opposite the two longitudinal legs (224, 225), the holder 220 is provided with a proximal shaft 226 extending from the back wall 221 in the proximal direction. At its distal end, where it is connected to the proximal edge of the back wall 221, the shaft 226 is provided with a circular rim 227.

Still with reference to FIGS. 19A and 19B, the damping gear wheel 230 comprises a circular plate 231 bearing a cogwheel 232 provided with circumferentially distributed outer teeth 233. The circular plate 231 is fixed with respect to the holder 220. The cogwheel 232 is allowed to rotate with respect to the circular plate 231 around its rotation axis 234, the rotation of the cogwheel 232 being controlled so as to be reduced by means of cooperation between a lubricant such as grease and the circular plate 231.

With reference to FIGS. 19A and 19B, the sensitive indicator 240 comprises a tubular part 241 provided at its proximal end with an inner radial rim 241a. The sensitive indicator 240 is further provided with a longitudinal leg 242 extending from the distal end of the tubular part 241 in the distal direction, the longitudinal leg 242 bearing a ratchet rail 243 provided with a plurality of notches 244. The longitudinal leg 242 further comprises near its distal end a recess 245 located opposite to the ratchet rail 243. At the proximal end of the tubular part 241 and laterally spaced with respect to the longitudinal axis of said tubular part 241, extends a shaft portion 246 in the proximal direction. The shaft portion 246 is provided at its proximal end with a rounded bump 247.

On FIGS. 19A and 19B, the controlling means and temporizing means assembly 210 is in a before use position, preloaded and ready to be triggered for producing a sensitive indication in a delayed manner. In this before use position, the sensitive indicator 240 is mounted on the holder 220 by means of shaft 226 of the holder 220 being received within the tubular part 241 of the sensitive indicator 240, the distal end of the tubular part 241 bearing onto the proximal edge of the back wall 221. The helical spring 250 is received within the tubular part 241, where it surrounds the shaft 226. As appears from FIG. 19B, the distal end of the helical spring 250 bears on the circular rim 227 of the holder 220 and the proximal end of the helical spring 250 bears on the inner radial rim 241a of the tubular part 241. In this preloaded position of the controlling means and temporizing means assembly 210, the helical spring 250 is in a stressed state, tending naturally to separate the sensitive indicator 240 from the holder 220. Nevertheless, the sensitive indicator 240 is maintained fixed in translation with respect to the holder 220 by means of front peg 224b of the first longitudinal leg 224 of the holder 220 being engaged in the recess 245 of the longitudinal leg 242 of the sensitive indicator 240. As appears also from FIG. 19A, the notches 244 of the ratchet rail 243 of the sensitive indicator 240 face the teeth 233 of the cogwheel 232 so as to be able to cooperate with them for rotating the cogwheel 232.

The functioning of the controlling means and temporizing means assembly 210 will now be explained with respect to FIGS. 20-21B, in which the controlling means and temporizing means assembly 210 has been fixed to a device 201 differing from device 1 of FIGS. 1A-17B mainly by the shape of the proximal region of the plunger rod 20. The plunger rod 20 of the device 201 of FIGS. 20-21B differs from that of FIGS. 1A-17B by the presence of a side projection 28 located at its proximal end and visible on FIG. 20. Concerning the rest of the device 201, the references designating the same elements as in FIGS. 1A-17B have been maintained.

As appears from FIG. 20, the controlling means and temporizing means assembly 210 is fixed onto the support 60 of the device 201 by means of hooks 223 being snap-fitted into engaging surfaces (not visible on the Figures) located on lateral walls 62 of the support 60. The controlling means and temporizing means assembly 210 is assembled on the support 60 in its preloaded state as shown on FIGS. 19A and 19B. Device 201 operates in the same manner as device 1 of FIGS. 1A-17B, and the controlling means and temporizing means assembly 210 remains in its preloaded state from the storage position of the device 201 until the end of the injection step: in other words, the operations described from FIG. 1A to FIG. 16A for device 1 are also valid for device 201.

On FIG. 20 is further shown partially and in dot line an outer shell 400 surrounding the device 201. Such an outer shell 400 protects the various elements constituting the device 201 and cancels from the user's view all these elements and their arrangement so as to render the device simpler and more friendly to the user. The outer shell 400 is provided at its proximal end 400a with a proximal hole 410 for the user to be able to activate the triggering means, namely to push distally on the button 90. The outer shell 400 is also provided at its distal end 400b with a distal hole 420 in order to let the needle protection means and the needle exit from the outer shell 400 for operation of the device. As shown on FIG. 20, an inner space 430 is present at the proximal end 400a of the outer shell 400, located between the rounded bump 247 of the sensitive indicator 240 and the distal face of a transversal wall 440 forming the proximal end 400a of the outer shell 400.

The controlling means and temporizing means assembly 210 is triggered at the end of the injection step, when the stopper, pushed distally by the plunger rod 20, comes close to the distal end of the syringe. This position is shown on FIG. 21A: at this moment, the side projection 28 of the plunger rod 20, which moves distally under the action of the first helical spring 8 tending to reach a less stressed state, comes in contact with the side peg 224a of the first longitudinal leg 224 of the holder 220 of the controlling means and temporizing means assembly 210, and deflects it. For clarity's sake, the outer shell 400 has not been shown, or is only partially shown, on FIGS. 21A and 21B.

By deflecting the side peg 224a of the first longitudinal leg 224 of the holder 220, the side projection 28 of the plunger rod 20 disengages the front peg 224b of the first longitudinal leg 224 of the holder 220 from the recess 245 of the longitudinal leg 242 of the sensitive indicator 240, thereby freeing the helical spring 250 of the controlling means and temporizing means assembly 210. The helical spring 250 expands in order to reach a less stressed state and pushes proximally on the sensitive indicator 240 which is moved in the proximal direction, as shown on FIG. 21B. During this movement, the notches 244 of the ratchet rail 243 of the sensitive indicator 240 cooperate with the teeth 233 of the cogwheel 232 which rotates. The rotation of the cogwheel 232 being controlled so as to be reduced as explained above, the distal movement of the ratchet rail 243 and thus of the shaft portion 246 and rounded bump 247 of the sensitive indicator 240 is dampened, so that the movement of the rounded bump 247 from its distal position, shown on FIG. 21A to its proximal position, shown on FIG. 21B, takes a certain time. When the rounded bump 247 reaches its proximal position after having traveled in inner space 430, it comes in contact with the distal face of the transversal wall 440 of the outer shell 400 (partially shown on FIG. 21B) and produces a sensitive indication, such as a sound. When the user hears this sound, he knows that substantially all the product has been injected and that he can remove the device 201 from the injection site with no risk. The delay between the moment the controlling means and temporizing means assembly 210 is triggered (FIG. 21A) and the moment the contact between the rounded bump 247 and the transversal wall 440 produces a sound ensures that substantially all the product has been injected and that the user will not remove the device from the injection site too early.

In the example shown, the sensitive indication is therefore a sound indication. Alternatively or in combination, the sensitive indication could be a visual indication or a tactile indication. For example, the transversal wall 440 of the outer shell 400 could be made of a transparent material allowing the user to see the rounded bump 247 once it has reached its proximal position. In such a case, the sensitive indicator would produce a visual indication that the device may be removed from the injection site. Alternatively or in combination, the outer shell 400 may be provided with a hole in the transversal wall 440, allowing the rounded bump 247 to be felt by the hand of the user. In such a case, the sensitive indicator would produce a tactile indication that the device may be removed from the injection site. In embodiments not shown, the rounded bump 247 may comprise a light that may be caused to be switched on when all the product has been expelled from the syringe.

With reference to FIG. 22 is shown an alternative embodiment of the controlling means and temporizing means assembly of FIGS. 19A and 19B. The assembly 210 of FIG. 22 differs from that of FIGS. 19A and 19B in that the distal region of the longitudinal leg 242 of the sensitive indicator 240 is further provided with side pins 248 (four on the example shown) able to cooperate with the front rim 225a of the second longitudinal leg 225 of the holder 220, when the sensitive indicator 240 moves proximally as explained above. The sensitive indicator 240 therefore produces a repeated sound, produced by the pins 248 coming in contact with, and escaping from, the front rim 225a of the second longitudinal leg 225 of the holder 220.

With respect to FIGS. 23A-24B is shown an alternative embodiment of a controlling means and temporizing means assembly for the device of the invention. The controlling means and temporizing means assembly 310 of FIGS. 23A-24B comprises a holder 320 intended to be fixed to the support 60 of device 201 of FIGS. 21A-21B. The holder 320 bears a sensitive indicator 340 intended to move with respect to the holder 320 once the controlling means and temporizing means assembly 310 is triggered.

With reference to FIGS. 23A and 23B, the holder 320 comprises lateral arms 321 provided with hooks 323 intended to be snap-fitted on the support 60 of device 201, as shown on FIGS. 24A and 24B, and in the same manner as described for FIGS. 21A-21B. The holder 320 comprises a piston 322 provided at its proximal end with a stopper 324 in which are arranged two longitudinal holes 324a. The holder 320 further comprises two lateral wall portions 325, distally spaced from the lateral arms 321. Each lateral wall portion 325 is provided in its proximal region with a plurality (three on the example shown) of inner teeth 326, and at its distal end with an inner peg 327.

Still with reference to FIGS. 23A and 23B, the sensitive indicator 340 is under the form of a tubular barrel 341 open at its distal end and closed at its proximal end by a shaft 342 extending in the proximal direction. The tubular barrel 341 is provided at its proximal end with an inner rim 341a forming an abutment surface. The sensitive indicator 340 is further provided at the distal end of the tubular barrel 341 with a transversal wall 343 from which two parallel longitudinal legs 344 extend in the distal direction. Each longitudinal leg 344 is provided at its distal end with an outer peg 345.

In the preloaded state of the controlling means and temporizing means assembly 310, as shown on FIGS. 23A and 23B, the piston 322 and the stopper 324 of the holder 320 are received within the tubular barrel 341 of the sensitive indicator 340. A helical spring 350 in a stressed state is lodged within said tubular barrel 341, with its distal end bearing on the stopper 324 and its proximal end bearing on the abutment surface formed by the inner rim 341a of the tubular barrel 341. The helical spring 350 naturally tends to separate the holder 320 from the sensitive indicator 340. Nevertheless, in the preloaded state of the controlling means and temporizing means assembly 310, the sensitive indicator 340 is maintained fixed with respect to the holder 320 by means of outer pegs 345 of the sensitive indicator 340 being in proximal abutment against inner pegs 327 of lateral wall portions 325 of the holder 320.

As shown on FIGS. 24A and 34B, the controlling means and temporizing means assembly 310 is mounted on the support 60 of a device 301 identical to that of FIGS. 21A and 21B. In this embodiment, the plunger rod 20 of device 201 of FIGS. 24A and 24B comprises two side projections 28 at its proximal end, one on each side of the plunger rod 20.

Like for the FIGS. 21A and 21B, the controlling means and temporizing means assembly 310 is triggered at the end of the injection step, when the stopper, pushed distally by the plunger rod 20, comes close to the distal end of the syringe. This position is shown on FIG. 24A: at this moment, the side projections 28 (only one is visible on FIG. 24A) of the plunger rod 20, which moves distally under the action of the first helical spring (not visible on FIG. 24a) tending to reach a less stressed state, come in contact with the outer pegs 345 of the longitudinal legs 344 of the sensitive indicator 340 of the controlling means and temporizing means assembly 310, and deflect them. For clarity's sake, the outer shell 300 has not been shown on FIGS. 24A and 24B.

The outer pegs 345 are therefore disengaged from inner pegs 327 of lateral wall portions 325 of the holder 320, and the helical spring 350 is free to expand towards a less stressed state. Expansion of the helical spring 350 causes the sensitive indicator 340 to move proximally. This movement is dampened by the presence of grease which is sheared through the longitudinal holes 324a of the stopper 324, so that the movement of the sensitive indicator 340, from its distal position shown on FIG. 24A, to its proximal position, shown on FIG. 24B, takes a certain time. The proximal end of the shaft 342 then comes in contact with the distal face of the transversal wall 440 of the outer shell 400 (as shown on FIG. 21B) and produces a sensitive indication, such as a sound. When the user hears this sound, he knows that substantially all the product has been injected and that he can remove the device from the injection site with no risk. The delay between the moment the controlling means and temporizing means assembly 310 is triggered (FIG. 24A) and the moment the contact between the shaft 342 and the transversal wall 440 produces a sound ensures that substantially all the product has been injected and that the user will not remove the device 301 from the injection site too early. Like for the previous embodiment of FIGS. 19A-21B, the sensitive indicator 340 could produce a sound, visual and/or tactile indication of the fact that the device 201 may be removed from the injection site with no risk.

With reference to FIG. 26 is shown an alternative embodiment for the plunger rod of device of FIGS. 1A-24B, provided with dampening means for reducing the rate with which the syringe 2 moves from its first position to its second position, under the effect of the first helical spring 8. With reference to this Figure, the plunger rod 520 comprises a first part 520a comprising a shaft 521, a bridge 522, longitudinal lodging 523 for accommodation of the first helical spring 8, semi-circular recess 525, oblique wall 526, distal leg 527 and rim 527a similar to bridges 22, longitudinal lodging 23, semi-circular recess 25, oblique wall 26, distal leg 27 and rim 27a of FIGS. 3A-3C. The plunger rod 520 further comprises a second part 520b comprising a tubular rod 528, open at its proximal end 528a and closed at its distal end 528b, capable of receiving the shaft 521. The closed distal end 528b of tubular rod 528 is intended to cooperate with the stopper 6. A helical spring 529 is lodged within the tubular rod 528 so as to surround the shaft 521. The helical spring 529 bears at its distal end on an inner rim 528c of tubular rod 528 and at its proximal end on the distal face of bridge 522. The helical spring 529 is in a stressed state before any insertion step, and it is maintained in said stressed state by means of a proximal tooth 528d of tubular rod 528 being in distal abutment on a proximal face of bridge 522. When the distal movement of plunger rod 520 is triggered in the manner already described above for FIGS. 1A-17B under the expansion of first helical spring 8, the distal movement of first part 520a of the plunger rod 520 causes the compression of helical spring 529 towards a more stressed state than its initial stressed state. As a consequence, the first helical spring 8 needs to overcome the additional resistance caused by the compression of helical spring 529, and the rate with which the syringe 2 moves from its first position to its second position is therefore reduced. The helical spring 529 acts as a dampening means for reducing the rate with which the syringe 2 moves from its first position to its second position, under the effect of the first helical spring 8. Such embodiments allow reducing the effect of the shock felt on his skin by the patient and produced by the syringe 2 coming in contact with his skin, when the needle is inserted into the injection site.

The invention claimed is:

1. A device for injection of a product into an injection site, said device comprising:
   a housing having a longitudinal axis A,
   a container located within the housing, said container capable of holding the product to be injected, said container including a proximal end and a distal end,
   a stopper located at the proximal end of the container for substantially closing the proximal end of the container, said stopper capable of being moved in a distal direction within the container to expel the product to be injected,
   a needle located at the distal end of the container, said needle configured to allow the product to exit there through, said container being movable with respect to said housing between a first position, in which the needle does not extend beyond a distal end of the housing, and a second position, which is distally spaced with respect to said first position, in which the needle extends beyond the distal end of the housing,
   a biasing member, coupled to said container and to said housing during movement of the container at least from said first position to said second position, said biasing member designed for exerting a distal force to said container so as to move said container from the first position to the second position when the biasing member transitions from a first state to a second state, wherein said second state is less stressed than said first state,
   a retaining device coupled to said container and to said housing when the container is in the first position, for releasably maintaining said biasing member in the first state, said retaining device being capable of moving from a passive condition, in which the retaining device maintains said biasing member in the first state, to an active condition, in which said biasing member is free to expand to its second state,
   a trigger capable of moving said retaining device from its passive condition to its active condition,
   wherein
   said retaining device comprises a lever member having a rotatable cylinder part and at least a radial projection extending from said cylinder part, said radial projection being in a first angular position when said retaining device is in its passive condition, and said radial projection being in a second angular position, which is different from said first angular position, when said retaining device is in its active condition, and wherein said rotatable cylinder part is included in a transversal plane of said longitudinal axis A.

2. The device of claim 1, wherein said biasing member is a spring linked to said stopper via a plunger rod, said device further comprising a releasable maintaining member for maintaining said container fixed with respect to said plunger rod when said spring transitions from its first state to its second state, said maintaining member being released when said spring reaches its second state.

3. The device of claim 2, wherein said maintaining member comprises a hook fixed with respect to said container, said hook trapping a rim located on said plunger rod, wherein the rim is only allowed to escape from said hook under the force of the spring when said container has reached its second position and said spring is in its second state.

4. The device of claim 2, wherein the cylinder part of the lever member is rotatably received within a recess of said plunger rod, said radial projection is engaged within an abutment surface fixed with respect to said housing when said radial projection is in its first angular position, and said radial projection is disengaged from said abutment surface when said radial projection is in its second angular position.

5. The device of claim 4, wherein said trigger comprises a button mounted in sliding translation with respect to said housing, said button comprising a pushing surface accessible to a user, said button further comprising a sloped surface capable of cooperating with said radial projection for rotating said cylinder part and moving said radial projection from its first angular position to its second angular position, upon application of a pushing force to said pushing surface.

6. The device of claim 1, wherein, in its first angular position, the radial projection extends in the distal direction.

7. The device of claim 6, wherein said button is mounted in sliding translation with respect to said housing along a direction parallel to said longitudinal axis A, said button further comprising a sloped surface, said sloped surface thereby moving said radial projection out of the distal direction towards its second angular position when cooperating with said radial projection.

8. The device of claim 1, further comprising: a locking member for preventing said trigger from moving said retaining device from its passive condition to its active condition, said locking member being releasable, and
   a deactivating device for releasing the locking member.

9. The device of claim 5, wherein the locking member comprises a movable surface of said device, said surface being movable between a first position, in which said surface faces said radial projection so as to prevent cooperation between said radial projection and said sloped surface, to a second position, in which said surface is released and does not face said radial projection, thereby allowing cooperation between said radial projection and said sloped surface.

10. The device of claim 8, wherein said deactivating device is capable of going from a storage position, in which it does not release the locking member, to an active position in which it releases the locking member and the trigger may be activated, the device further comprises a storage elastic return member for urging said deactivating device back in its storage position as long as the trigger has not been activated.

11. The device of claim 1, further comprising:
    a fixing member for maintaining said container in its second position with respect to said housing, and
    an urging member coupled to said stopper and to said housing when said container is in its second position, said urging member configured for distally moving said stopper when transitioning from a first state to a second state, said second state being less stressed than said first state, thereby resulting in injection of the product.

12. The device of claim 2, wherein said spring is further capable of transitioning from its second state to a third state, during which said spring moves the stopper distally, said third state being less stressed than said second state, and wherein said spring forms both said biasing member and said urging member.

13. The device of claim 11, wherein the fixing member comprises a peg fixed with respect to said container and a window is located on said housing, said peg being locked within said window when said container is in its second position with respect to said housing.

14. The device of claim 1, further comprising:
a needle protection member, at least partially received within said housing, and movable with respect to said housing when said container is fixed in its second position with respect to said housing between an insertion position, in which a distal tip of the needle extends beyond the distal end of the needle protection member, and a final position, in which the distal tip of the needle does not extend beyond the distal end of the needle protection member, and
an elastic return member, coupled to said needle protection member and to said container, and designed for automatically moving said needle protection member from its insertion position to its final position, upon removal of the device from an injection site by a user.

15. The device of claim 8, wherein, in the first position of the container with respect to the housing, said needle protection member is movable with respect to said housing between a storage position and a use position, said use position being proximally spaced with respect to said storage position, and wherein at least part of said needle protection means forms said deactivating device.

16. The device of claim 15, wherein at least part of said needle protection member further forms said locking member.

17. The device of claim 1, wherein said biasing member is positioned so as to produce a distal force along an axis parallel to said longitudinal axis A, said device further comprising a linking member coupled to said biasing member and to said container, said linking member being shaped and dimensioned so as to transmit said distal force to said container.

18. The device of claim 2, wherein said plunger rod forms said linking member, said plunger rod comprising a shaft aligned on said longitudinal axis A, said shaft being provided at its distal end with said stopper, a bridge linking a proximal end of said shaft to a proximal end of a lateral tubular lodging parallel to said longitudinal axis A and receiving said spring, said spring being in distal abutment on a distal transversal wall of said tubular lodging and being in proximal abutment on a proximal transversal wall fixed with respect to said housing.

19. The device of claim 4, wherein the recess of said plunger rod is located on a distal face of said distal transversal wall of said tubular lodging.

20. The device of claim 1, further comprising a controlling member designed for producing a sensitive indication when said stopper reaches a distal end of said container.

21. The device of claim 20, further comprising a temporizing member designed for delaying the production of said sensitive indication once said stopper has reached a distal end of said container, thereby ensuring that indication to the user that injection of the product is completed is only given once the product is substantially expelled from the container.

22. The device of claim 2, wherein the temporizing member comprises a holder fixed with respect to said housing and a sensitive indicator movable with respect to said holder between a distal position, in which the indicator does not produce said sensitive indication, and a proximal position, in which the indicator produces said sensitive indication, said temporizing member further comprising:
an indicator biasing member coupled to said holder and to said sensitive indicator, said indicator biasing member designed for urging said sensitive indicator in its proximal position when transitioning from a compressed state to an expanded state,
indicator retaining members for maintaining said indicator biasing member in its compressed state,
wherein said indicator retaining members are released by cooperation of said indicator retaining members with at least a part of said plunger rod at the end of the injection step.

23. The device of claim 1, further comprising an outer shell surrounding the whole device, said outer shell being provided with at least a first hole for access to the trigger by the user, and at least a second hole for exit of the needle and/or of the needle protection means.

24. The device of claim 22, wherein at least a part of the sensitive indicator interacts with at least a part of a wall of said outer shell, when said sensitive indicator is in its proximal position, in order to produce said sensitive indication.

25. The device of claim 1, further comprising a removable distal cap for closing the distal end of said housing before use, said device further comprising a tamper evident member for informing the user that the distal cap has already been removed at least once before having been replaced on said distal end of said housing.

26. The device of claim 1, further comprising a dampening member for reducing the rate with which said container transitions from its first position to its second position, under the effect of said biasing member.

27. The device of claim 14, wherein said device is under the form of two autonomous connectable parts, said connectable parts comprising a motor part and a housing part,
said motor part comprising at least said biasing member, said retaining device, said trigger, and said urging member,
said housing part comprising at least said housing, said deactivating member, said fixing member, said needle protection member, and said elastic return member,
said locking member being located on one of said motor part and housing part, said device further comprising a connecting member for connecting said motor part to said housing part at the time of use.

28. The device of claim 27, wherein said locking member is located on said housing part, said motor part further comprises a temporary lock, for maintaining the retaining member in its passive condition when said motor part is not connected to said housing part, said temporary lock being removed from said motor part once said motor part is connected to said housing part, said temporary lock being then replaced by said locking member present on the housing part.

29. The device of claim 28, wherein said locking member comprises at least a surface of said needle protection member.

* * * * *